(12) United States Patent
Apte et al.

(10) Patent No.: US 11,137,408 B2
(45) Date of Patent: Oct. 5, 2021

(54) GDF15 IN GLAUCOMA AND METHODS OF USE THEREOF

(71) Applicant: Washington University, St. Louis, MO (US)

(72) Inventors: Rajendra S. Apte, St. Louis, MO (US); Jun Yoshino, St. Louis, MO (US)

(73) Assignee: Washington University, St. Louis, MO (US)

( * ) Notice: Subject to any disclaimer, the term of this patent is extended or adjusted under 35 U.S.C. 154(b) by 214 days.

(21) Appl. No.: 16/073,726

(22) PCT Filed: Jan. 30, 2017

(86) PCT No.: PCT/US2017/015643
§ 371 (c)(1),
(2) Date: Jul. 27, 2018

(87) PCT Pub. No.: WO2017/132673
PCT Pub. Date: Aug. 3, 2017

(65) Prior Publication Data
US 2019/0011458 A1 Jan. 10, 2019

Related U.S. Application Data

(60) Provisional application No. 62/289,030, filed on Jan. 29, 2016.

(51) Int. Cl.
| | | |
|---|---|---|
| *G01N 33/543* | (2006.01) | |
| *G01N 33/68* | (2006.01) | |
| *C12Q 1/6883* | (2018.01) | |
| *C07K 14/475* | (2006.01) | |

(52) U.S. Cl.
CPC ....... *G01N 33/6893* (2013.01); *C07K 14/475* (2013.01); *C12Q 1/6883* (2013.01); *C12Q 2600/106* (2013.01); *C12Q 2600/112* (2013.01); *C12Q 2600/158* (2013.01); *G01N 2333/52* (2013.01); *G01N 2800/168* (2013.01); *G01N 2800/52* (2013.01)

(58) Field of Classification Search
CPC .......... G01N 33/6893; G01N 2333/52; G01N 2800/168; G01N 2800/52
See application file for complete search history.

(56) References Cited

U.S. PATENT DOCUMENTS

| | | | |
|---|---|---|---|
| 6,566,495 B1 | 5/2003 | Fodor et al. | |
| 7,939,313 B2 | 5/2011 | Heyduk et al. | |
| 2009/0239947 A1 | 9/2009 | Weixang et al. | |
| 2017/0137506 A1* | 5/2017 | Gyuris | ................. A61P 13/12 |
| 2018/0224431 A1* | 8/2018 | Guerreiro | .......... G01N 33/5014 |

FOREIGN PATENT DOCUMENTS

| | | | | |
|---|---|---|---|---|
| EP | 2103943 | * | 3/2008 | ............. G01N 33/68 |
| EP | 2770326 A1 | | 8/2014 | |
| WO | 2013012648 A1 | | 1/2013 | |
| WO | 2013113008 A1 | | 8/2013 | |
| WO | 2015171457 A1 | | 11/2015 | |
| WO | 2017132673 A1 | | 8/2017 | |

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, 2014, pp. 1-7. (Year: 2014).*
Blumberg, D. et al., "Emerging risk factors for glaucoma onset and progression," Progress in Brain Research, Jan. 2015, pp. 81-101, vol. 221.
Extended European Search Report from related European Patent Application No. 17745087.1, dated Sep. 3, 2019, 7 pgs.
Adela, R. et al., "GDF-15 as a Target and Biomarker for Diabetes and Cardiovascular Diseases: A Translational Prospective," J. Diabetes Res., 2015, pp. 1-14, vol. 2015, Article ID 490842, Hindawi Publishing Corporation.
Ban, N. et al., "GDF15 is elevated in mice following retinal ganglion cell death and in glaucoma patients," JCI Insight, 2017, pp. 1-14, vol. 2, No. 9, e91455.
Bucknall, M. et al., "Practical Quantitative Biomedical Applications of MALDI-TOF Mass Spectrometry," J. Am. Soc. Mass Spectrom., 2002, pp. 1015-1027, vol. 13, Elsevier Science Inc.
Charalambous, P. et al., "Regulation and effects of GDF-15 in the retina following optic nerve crush," Cell Tissue Res., Jul. 2013, pp. 1-8, vol. 353, Springer-Verlag Berlin Heidelberg.
Chen, Q. et al., "Apo2L/TRAIL and Bcl-2-related proteins regulate type I interferon-induced apoptosis in multiple myeloma," Blood, Oct. 1, 2001, pp. 2183-2192, vol. 98, No. 7.
GenBank Accession No. NM_004864.3, "*Homo sapiens* growth differentiation factor 15 (GDF15), mRNA," dated Sep. 28, 2018, 4 pgs.
GenBank Accession No. NP_004855.2, "Growth/differentiation factor 15 preproprotein [*Homo sapiens*]," dated Sep. 28, 2018, 3 pgs.
Gobom, J. et al., "Detection and Quantification of Neurotensin in Human Brain Tissue by Matrix-Assisted Laser Desorption/Ionization Time-of-Flight Mass Spectrometry," Anal. Chem., Jul. 5, 2000, pp. 3320-3326, vol. 72, No. 14.
International Search Report and Written Opinion dated Apr. 5, 2017 from Appl. Serial No. PCT/US2017/015643; 12 pgs.
Mirgorodskaya, E. et al., "Characterization of Protein Glycosylation by MALDI-TOFMS," Methods Mol. Biol., 2000, pp. 273-292, vol. 146, Humana Press Inc.
Muralidharan, A. et al., "Growth Differentiation Factor-15-Induced Contractile Activity and Extracellular Matrix Production in Human Trabecular Meshwork Cells," Invest. Ophthalmol. Vis. Sci., Dec. 2016, pp. 6482-6495, vol. 57, No. 15.

(Continued)

*Primary Examiner* — Gary Counts
(74) *Attorney, Agent, or Firm* — Polsinelli PC

(57) ABSTRACT

The present disclosure provided methods for determining the severity of glaucoma using the expression levels of GDF15. Determining the severity of glaucoma aids in treatment decisions.

8 Claims, 22 Drawing Sheets
(4 of 22 Drawing Sheet(s) Filed in Color)

(56) References Cited

OTHER PUBLICATIONS

Rockett, J. et al., "DNA arrays: technology, options and toxicological applications," Xenobiotica, 2000, pp. 155-177, vol. 30, No. 2, Taylor & Francis Ltd.

Zhong, X. et al., "Evaluation of MUC1 and EGP40 in bone marrow and peripheral blood as a marker for occult breast cancer," Arch. Gynecol. Obstet., Jan. 2001, pp. 177-181, vol. 264, No. 4, abstract only.

Office Action dated Feb. 16, 2021 from related Japanese Patent Application No. 2018-559172; 10 pgs., with English translation, English portions only.

Office Action dated Apr. 6, 2021 from related Chinese Patent Application No. 201780021280.6; 10 pgs., English portions only.

* cited by examiner

# GDF15 IN GLAUCOMA AND METHODS OF USE THEREOF

CROSS REFERENCE TO RELATED APPLICATIONS

This application claims the benefit of U.S. Provisional Application No. 62/289,030, filed Jan. 29, 2016, the disclosure of which is hereby incorporated by reference in its entirety.

GOVERNMENTAL RIGHTS

This invention was made with government support under EY019287 awarded by the National Institutes of Health. The government has certain rights in the invention.

FIELD OF THE INVENTION

The present disclosure provided methods for determining the severity of glaucoma using the expression levels of GDF15. Determining the severity of glaucoma aids in treatment decisions.

BACKGROUND OF THE INVENTION

Glaucoma is a group of diseases that damage the eye's optic nerve and can result in vision loss and blindness. However, with early detection and treatment, the eyes can be protected against serious vision loss. There are currently no available biomarkers which detect glaucoma severity or progression. Tgfb2 can cause glaucoma, but it is not a biomarker for glaucoma. Currently, treatment for glaucoma is decided based on intraocular pressure (IOP) and perimetry. However, IOP has a huge variation from patient to patient and perimetry is a subjective test. Thus, a biomarker to aid in treatment decisions for glaucoma is needed.

SUMMARY OF THE INVENTION

In an aspect, the disclosure provides a method of determining glaucoma severity in a subject diagnosed with glaucoma. The method comprises: (a) measuring the amount of gdf15 nucleic acid or GDF15 protein in a biological sample obtained from the subject; (b) comparing the amount of gdf15 nucleic acid or GDF15 protein in the biological sample to a reference value; and (c) determining the severity of glaucoma based on the amount of gdf15 nucleic acid or GDF15 protein relative to the reference value.

In another aspect, the disclosure provides a method of determining treatment in a subject diagnosed with glaucoma. The method comprises: (a) measuring the amount of gdf15 nucleic acid or GDF15 protein in a biological sample obtained from the subject; (b) comparing the amount of gdf15 nucleic acid or GDF15 protein in the biological sample to a reference value, wherein the amount of gdf15 nucleic acid or GDF15 protein above the reference value indicates glaucoma severity; and (c) determining treatment of the subject based on the detected glaucoma severity.

In still another aspect, the disclosure provides a method of monitoring glaucoma progression in a subject. The method comprises: (a) measuring the amount of gdf15 nucleic acid or GDF15 protein in a first biological sample obtained from the subject; (b) measuring the amount gdf15 nucleic acid or GDF15 protein in a second biological sample obtained from the subject at a later time; (c) comparing the amount of gdf15 nucleic acid or GDF15 protein in the first biological sample to the amount of gdf15 nucleic acid or GDF15 protein in the first biological sample; and (d) determining glaucoma progression if the amount of gdf15 nucleic acid or GDF15 protein in the second biological sample is increased relative to the amount of gdf15 nucleic acid or GDF15 protein in the first biological sample.

In still yet another aspect, the disclosure provides a method of monitoring response to glaucoma treatment in a subject. The method comprises: (a) measuring the amount of gdf15 nucleic acid or GDF15 protein in a first biological sample obtained from the subject; (b) treating the subject; (c) measuring the amount gdf15 nucleic acid or GDF15 protein in a second biological sample obtained from the subject at a later time; (d) comparing the amount of gdf15 nucleic acid or GDF15 protein in the first biological sample to the amount of gdf15 nucleic acid or GDF15 protein in the first biological sample; and (e) determining response to treatment if the amount of gdf15 nucleic acid or GDF15 protein in the second biological sample is decreased relative to the amount of gdf15 nucleic acid or GDF15 protein in the first biological sample.

BRIEF DESCRIPTION OF THE FIGURES

The application file contains at least one drawing executed in color. Copies of this patent application publication with color drawing(s) will be provided by the Office upon request and payment of the necessary fee.

(FIG. 5A) gdf1; (FIG. 5B) gdf2; (FIG. 5C) gdf3; (FIG. 5D) gdf5; (FIG. 5E) gdf6; (FIG. 5F) gdf7; (FIG. 5G) gdf8; (FIG. 5H) gdf9; (FIG. 5I) gdf10; and (FIG. 5J) gdf11.

DETAILED DESCRIPTION OF THE INVENTION

Figure 1:
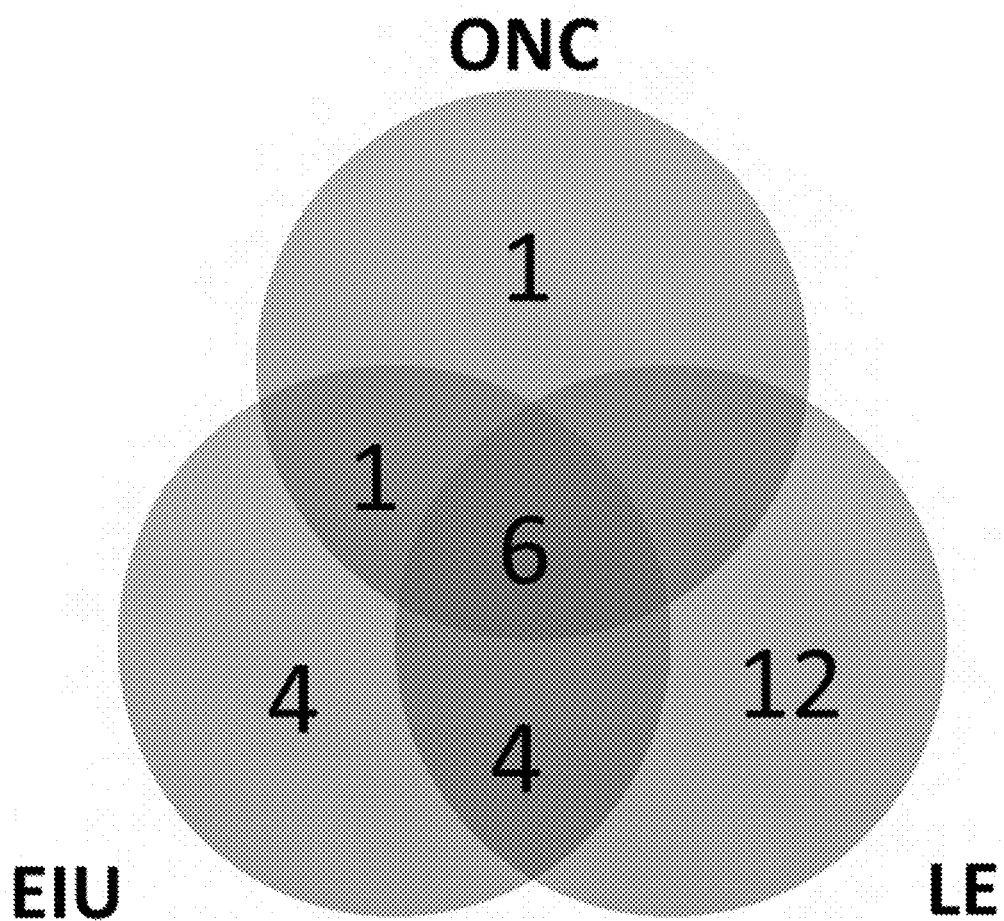
FIG. 1 depicts a Venn diagram showing the upregulated genes that overlap between the optic nerve crush model (ONC), the endotoxin-induced uveitis model (EIU) and the light exposure induced retinal degeneration model (LE).

The present disclosure provides a statistically significant relationship between increases in aqueous humor concentrations of GDF15 protein and an increase in severity of glaucoma. Growth/differentiation factor 15 (GDF15) is a protein belonging to the transforming growth factor beta superfamily. GDF15 may also be referred to as growth/differentiation factor 15, TGF-PL, MIC-1, PDF, PLAB, NAG-1, and PTGFB. The amino acid sequence of GDF15 can be found at GenBank Accession number NP_004855.2 and the mRNA sequence can be found at GenBank Accession number NM_004864.3. A skilled artisan would be able to determine the sequences based on the GenBank Accession number provided. It was unpredictable that GDF15 protein levels would be elevated in glaucoma which is due to chronic damage to retinal ganglion cells and that the elevation of GDF15 would specifically correlate with the grade of glaucoma. Surprisingly, GDF15 is the only specific gene that is upregulated with retinal ganglion cell injury. Accordingly, provided herein are methods that utilize this relationship to provide inventive means of determining glaucoma severity and aiding in treatment decisions.

Provided herein are methods for detecting gdf15 nucleic acid and GDF15 protein and their use in classifying the severity of glaucoma in a subject. Various aspects of these methods are described in more detail below.

I. METHODS

In an aspect, the disclosure provides a method to classify a subject based on the amount of gdf15 nucleic acid or GDF15 protein measured in a biological sample obtained from the subject. The method generally comprises (i) measuring the amount of gdf15 nucleic acid or GDF15 protein in the biological sample, (ii) comparing the amount of gdf15 nucleic acid or GDF15 protein in the biological sample to a reference value, and (iii) classifying the subject as having an increased or decreased amount gdf15 nucleic acid or GDF15 protein based on the amount gdf15 nucleic acid or GDF15 protein measured in the sample.

In another aspect, the disclosure provides a method to determine the severity of glaucoma in a subject diagnosed with glaucoma. The method generally comprises (i) measuring the amount gdf15 nucleic acid or GDF15 protein in a biological sample obtained from the subject, (ii) comparing the amount of gdf15 nucleic acid or GDF15 protein in the biological sample to a reference value, and (iii) determining the severity of glaucoma based on the amount of gdf15 nucleic acid or GDF15 protein relative to the reference value. Methods of diagnosing glaucoma in a subject are known in the art and may include, but are not limited to, measuring eye pressure (intraocular eye pressure (IOP), tonometry), inspecting eye's drainage angle (gonioscopy), inspecting the optic nerve (ophthalmoscopy), testing peripheral vision (visual field test, perimetry), and measuring the thickness of the cornea (pachymetry). In certain embodiments, the subject may not be diagnosed with glaucoma but is suspected of having glaucoma based on symptoms. Non-limiting examples of symptoms of glaucoma that may lead to a diagnosis include blind spots in the peripheral view, blurred vision, halos, mild headaches, eye pain, severe pain in the eye or forehead, redness of the eye, decreased vision, vision rainbows, nausea and/or vomiting. In other embodiments, the subject may not be diagnosed with glaucoma but is at risk of having glaucoma. Non-limiting examples of risk factors for glaucoma include high IOP, age greater than 60 years, African American or Hispanic, family history of glaucoma, medical conditions such as diabetes, heart disease, high blood pressure and sickle cell anemia, eye conditions such as nearsightedness, history of eye injury or certain types of eye surgery, early estrogen deficiency such as can occur after bilateral oophorectomy before age 43, and/or taking corticosteroid medications, especially eye-drops, for an extended time.

In general, the severity of glaucoma is determined based on the ICD-9 staging definitions. However, the present disclosure provides that the amount of gdf15 nucleic acid or GDF15 protein in a biological sample may be used to determine the severity of glaucoma. According to the ICD-9 staging definitions the severity of glaucoma may be mild or early-stage glaucoma (Grade I), moderate-stage glaucoma (Grade II) or severe-stage glaucoma, advanced-stage glaucoma, end-stage glaucoma (Grade III). Mild or early-stage glaucoma (Grade I) is defined as optic nerve abnormalities consistent with glaucoma but no visual field abnormalities on any white-on-white visual field test, or abnormalities present only on short-wavelength automated perimetry or frequency-doubling perimetry. Moderate-stage glaucoma (Grade II) is defined as optic nerve abnormalities consistent with glaucoma and glaucomatous visual field abnormalities in one hemifield, and not within 5 degrees of fixation. Severe-stage glaucoma, advanced-stage glaucoma, end-stage glaucoma (Grade III) is defined as optic nerve abnormalities consistent with glaucoma and glaucomatous visual field abnormalities in both hemifields, and/or loss within 5 degrees of fixation in at least one hemifield. Other staging systems known in the art may be used. A skilled artisan would be able to correlate the ICD-9 staging system with other staging systems. Accordingly, based on the amount of gdf15 nucleic acid or GDF15 protein in the biological sample a subject may be classified into Grade I, Grade II or Grade III glaucoma. Treatment decisions may then be made based on the stage of glaucoma.

In still another aspect, the disclosure provides a method of determining treatment of a subject diagnosed with glaucoma. The method generally comprises (i) measuring the amount gdf15 nucleic acid or GDF15 protein in a biological sample obtained from the subject, (ii) comparing the amount of gdf15 nucleic acid or GDF15 protein in the biological sample to a reference value, wherein the amount of gdf15 nucleic acid or GDF15 protein above the reference value indicates glaucoma severity, and (iii) determining treatment of the subject based on the detected glaucoma severity. In certain embodiments, the subject may not be diagnosed with glaucoma but is suspected of having glaucoma based on symptoms. In other embodiments, the subject may not be diagnosed with glaucoma but is at risk of having glaucoma.

Based on the amount of gdf15 nucleic acid or GDF15 protein in the biological sample a subject may be classified into Grade I, Grade II or Grade III glaucoma. Glaucoma may be treated with eye drops, pills, laser surgery, incisional surgery or a combination of these methods. The goal of any treatment is to prevent loss of vision, as vision loss from glaucoma is irreversible. Generally, eye drops are used to treat low grade glaucoma. If eye drops do not sufficiently control IOP, pills may be used in addition to eye drops. When medications do not achieve the desired results or have intolerable side effect, surgery may be the next option. Surgery may be laser surgery or incisional surgery. Laser surgery is viewed as an intermediate step between medication and incisional surgery. Non-limiting examples of laser surgery include argon laser trabeculoplasty (ALT), selective laser trabeculoplasty (SLT), laser peripheral iridotomy (LPI), and cycloablation. Non-limiting examples of incisional surgery include trabeculectomy, drainage implant surgery, nonpenetrating surgery, ExPress mini glaucoma shunt, Trabectome and canaloplasty. Based on the classification into Grade I, Grade II or Grade III based on the amount of gdf15 nucleic acid or GDF15 protein in a biological sample, the subject may be treated with eye drops, pills, laser surgery and/or incisional surgery.

In still yet another aspect, the disclosure provides a method for monitoring glaucoma in a subject. In such an embodiment, a method of detecting gdf15 nucleic acid or GDF15 protein may be used to assess the severity of gluacoma in a subject at one point in time. Then at a later time, the method of detecting gdf15 nucleic acid or GDF15 protein may be used to determine the change in severity of glaucoma in the subject over time. For example, the method of detecting gdf15 nucleic acid or GDF15 protein may be used on the same subject days, weeks, months or years following the initial determination of the amount of gdf15 nucleic acid or GDF15 protein. Accordingly, the method of detecting gdf15 nucleic acid or GDF15 protein may be used to follow a subject over time to determine when the risk of progressing to more severe disease is high thereby requiring treatment. Additionally, the method of detecting gdf15 nucleic acid or GDF15 protein may be used to measure the rate of disease progression. For example, a decreased amount of gdf15 nucleic acid or GDF15 protein may indicate an abatement of disease progression. Alternatively, an increased amount of gdf15 nucleic acid or GDF15 protein may indicate disease progression. Early assessment of the severity of glaucoma in the subject may reduce the development and/or progression of symptoms associated with glaucoma by enabling improved interventions or enabling earlier interventions.

Additionally, a method for monitoring glaucoma in a subject may also be used to determine the response to treatment. As used herein, subjects who respond to treatment are said to have benefited from treatment. Responses to treatment are measured in clinical practice using tests including, but not limited to, measuring eye pressure (intraocular eye pressure (IOP), tonometry), inspecting eye's drainage angle (gonioscopy), inspecting the optic nerve (ophthalmoscopy), testing peripheral vision (visual field test, perimetry), and measuring the thickness of the cornea (pachymetry). These tests are well known in the art and are intended to refer to specific parameters measured during clinical trials and in clinical practice by a skilled artisan. For example, a method to detect gdf15 nucleic acid or GDF15 protein may be performed on the biological sample of the subject prior to initiation of treatment. Then at a later time, a method to detect gdf15 nucleic acid or GDF15 protein may be used to determine the response to treatment over time. For example, a method to detect gdf15 nucleic acid or GDF15 protein may be performed on the biological sample of the same subject days, weeks, months or years following initiation of treatment. Accordingly, a method to detect gdf15 nucleic acid or GDF15 protein may be used to follow a subject receiving treatment to determine if the subject is responding to treatment. If the amount of gdf15 nucleic acid or GDF15 protein increases or remains the same, then the subject may not be responding to treatment. If the amount of gdf15 nucleic acid or GDF15 protein decreases, then the subject may be responding to treatment. These steps may be repeated to determine the response to therapy over time.

Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In certain embodiments, the animal is a rodent. In a preferred embodiment, the subject is human.

(a) Biological Sample

As used herein, the term "biological sample" refers to a sample obtained from a subject. Any biological sample containing GDF15 protein or gdf15 nucleic acid is suitable. Numerous types of biological samples are known in the art. Suitable biological sample may include, but are not limited to, tissue samples or bodily fluids. In some embodiments, the biological sample is a tissue sample such as a tissue biopsy. The biopsied tissue may be fixed, embedded in paraffin or plastic, and sectioned, or the biopsied tissue may be frozen and cryosectioned. In a specific embodiment, the biopsied tissue is retinal tissue. In other embodiments, the sample may be a bodily fluid. Non-limiting examples of suitable bodily fluids include aqueous humor. In a specific embodiment, the biological sample is aqueous humor. The fluid may be used "as is", the cellular components may be isolated from the fluid, or a fraction may be isolated from the fluid using standard techniques.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that the gdf15 nucleic acid or GDF15 protein can be accurately detected and the amount measured according to the disclosure. In a specific embodiment, the aqueous humor is collected at the beginning of surgery.

In some embodiments, a single sample is obtained from a subject to detect gdf15 nucleic acid or GDF15 protein in the sample. Alternatively, gdf15 nucleic acid or GDF15 protein may be detected in samples obtained over time from a subject. As such, more than one sample may be collected from a subject over time. For instance, 2, 3, 4, 5, 6, 7, 8, 9, 10, 11, 12, 13, 14, 15, 16 or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, 13, or 14 samples are collected from a subject over time. In other embodiments, 14, 15, 16 or more samples are collected from a subject over time.

When more than one sample is collected from a subject over time, samples may be collected every 1, 2, 3, 4, 5, 6, 7, 8, 9, 10, 11, 12 or more days. In some embodiments, a sample is collected about every 6 days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12 or more days. In still other embodiments, samples are collected a month apart, 3 months apart, 6 months apart, 1 year apart, 2 years apart, 5 years apart, 10 years apart or more.

(b) Detecting gdf15 Nucleic Acid or GDF15 Protein

Once a sample is obtained, it is processed in vitro to detect and measure the amount of gdf15 nucleic acid or GDF15 protein. All suitable methods for detecting and measuring an amount of gdf15 nucleic acid or GDF15 protein known to one of skill in the art are contemplated within the scope of the invention. Methods of detecting nucleic acid expression and protein expression are described in detail below.

i. Nucleic Acid Expression

In an embodiment, gdf15 nucleic acid expression may be measured to determine the amount of gdf15 nucleic acid in a biological sample. In a specific embodiment, gdf15 mRNA may be measured to determine the amount of gdf15 nucleic acid in a biological sample.

Methods for assessing an amount of nucleic acid expression in a sample are well known in the art, and all suitable methods for assessing an amount of nucleic acid expression known to one of skill in the art are contemplated within the scope of the invention. The term "amount of nucleic acid expression" or "level of nucleic acid expression" as used herein refers to a measurable level of expression of the nucleic acids, such as, without limitation, the level of messenger RNA (mRNA) transcript expressed or a specific variant or other portion of the mRNA, the enzymatic or other activities of the nucleic acids, and the level of a specific metabolite. The term "nucleic acid" includes DNA and RNA and can be either double stranded or single stranded. Non-limiting examples of suitable methods to assess an amount of nucleic acid expression may include arrays, such as microarrays, PCR, such as RT-PCR (including quantitative RT-PCR), nuclease protection assays and Northern blot analyses. In a specific embodiment, determining the amount of expression of a target nucleic acid comprises, in part, measuring the level of target nucleic acid mRNA expression.

In one embodiment, the amount of nucleic acid expression may be determined by using an array, such as a microarray. Methods of using a nucleic acid microarray are well and widely known in the art. For example, a nucleic acid probe that is complementary or hybridizable to an expression product of a target gene may be used in the array. The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In another embodiment, the amount of nucleic acid expression may be determined using PCR. Methods of PCR are well and widely known in the art, and may include quantitative PCR, semi-quantitative PCR, multiplex PCR, or any combination thereof. Specifically, the amount of nucleic acid expression may be determined using quantitative RT-PCR. Methods of performing quantitative RT-PCR are common in the art. In such an embodiment, the primers used for quantitative RT-PCR may comprise a forward and reverse primer for a target gene. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The amount of nucleic acid expression may be measured by measuring an entire mRNA transcript for a nucleic acid sequence, or measuring a portion of the mRNA transcript for a nucleic acid sequence. For instance, if a nucleic acid array is utilized to measure the amount of mRNA expression, the array may comprise a probe for a portion of the mRNA of the nucleic acid sequence of interest, or the array may comprise a probe for the full mRNA of the nucleic acid sequence of interest. Similarly, in a PCR reaction, primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art. Methods of extracting RNA from a biological sample are known in the art.

The level of expression may or may not be normalized to the level of a control nucleic acid. This allows comparisons between assays that are performed on different occasions.

ii. Protein Expression

In another embodiment, GDF15 protein expression may be measured to determine the amount of GDF15 protein in a biological sample. In a specific embodiment, GDF15 protein expression may be measured using an ELISA to determine the amount of GDF15 protein in a biological sample.

Methods for assessing an amount of protein expression are well known in the art, and all suitable methods for assessing an amount of protein expression known to one of skill in the art are contemplated within the scope of the invention. Non-limiting examples of suitable methods to assess an amount of protein expression may include epitope binding agent-based methods and mass spectrometry based methods.

In some embodiments, the method to assess an amount of protein expression is mass spectrometry. By exploiting the intrinsic properties of mass and charge, mass spectrometry (MS) can resolve and confidently identify a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can use mass spectrometry to look for the level of protein encoded from a target nucleic acid of the invention.

In some embodiments, the method to assess an amount of protein expression is an epitope binding agent-based method. As used herein, the term "epitope binding agent" refers to an antibody, an aptamer, a nucleic acid, an oligonucleic acid, an amino acid, a peptide, a polypeptide, a protein, a lipid, a metabolite, a small molecule, or a fragment thereof that recognizes and is capable of binding to a target gene protein. Nucleic acids may include RNA, DNA, and naturally occurring or synthetically created derivative.

As used herein, the term "antibody" generally means a polypeptide or protein that recognizes and can bind to an epitope of an antigen. An antibody, as used herein, may be a complete antibody as understood in the art, i.e., consisting of two heavy chains and two light chains, or may be any antibody-like molecule that has an antigen binding region, and includes, but is not limited to, antibody fragments such as Fab', Fab, F(ab')2, single domain antibodies, Fv, and single chain Fv. The term antibody also refers to a polyclonal antibody, a monoclonal antibody, a chimeric antibody and a humanized antibody. The techniques for preparing and using various antibody-based constructs and fragments are well known in the art. Means for preparing and characterizing antibodies are also well known in the art (See, e.g. Antibodies: A Laboratory Manual, Cold Spring Harbor Laboratory, 1988; herein incorporated by reference in its entirety).

As used herein, the term "aptamer" refers to a polynucleotide, generally a RNA or DNA that has a useful biological activity in terms of biochemical activity, molecular recognition or binding attributes. Usually, an aptamer has a molecular activity such as binging to a target molecule at a specific epitope (region). It is generally accepted that an aptamer, which is specific in it binding to a polypeptide, may be synthesized and/or identified by in vitro evolution methods. Means for preparing and characterizing aptamers, including by in vitro evolution methods, are well known in the art (See, e.g. U.S. Pat. No. 7,939,313; herein incorporated by reference in its entirety).

In general, an epitope binding agent-based method of assessing an amount of protein expression comprises contacting a sample comprising a polypeptide with an epitope binding agent specific for the polypeptide under conditions effective to allow for formation of a complex between the epitope binding agent and the polypeptide. Epitope binding agent-based methods may occur in solution, or the epitope binding agent or sample may be immobilized on a solid surface. Non-limiting examples of suitable surfaces include microtitre plates, test tubes, beads, resins, and other polymers.

An epitope binding agent may be attached to the substrate in a wide variety of ways, as will be appreciated by those in the art. The epitope binding agent may either be synthesized first, with subsequent attachment to the substrate, or may be directly synthesized on the substrate. The substrate and the epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, the epitope binding agent may be attached directly using the functional groups or indirectly using linkers.

The epitope binding agent may also be attached to the substrate non-covalently. For example, a biotinylated epitope binding agent may be prepared, which may bind to surfaces covalently coated with streptavidin, resulting in attachment. Alternatively, an epitope binding agent may be synthesized on the surface using techniques such as photopolymerization and photolithography. Additional methods of attaching epitope binding agents to solid surfaces and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, both of which are hereby incorporated by reference in their entirety).

Contacting the sample with an epitope binding agent under effective conditions for a period of time sufficient to allow formation of a complex generally involves adding the epitope binding agent composition to the sample and incubating the mixture for a period of time long enough for the epitope binding agent to bind to any antigen present. After this time, the complex will be washed and the complex may be detected by any method well known in the art. Methods of detecting the epitope binding agent-polypeptide complex are generally based on the detection of a label or marker. The term "label", as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, strepavidin, protein A, protein G, antibodies or fragments thereof, polyhistidine, $Ni2+$, Flag tags, myc tags, heavy metals, and enzymes (including alkaline phosphatase, peroxidase, and luciferase). Methods of detecting an epitope binding agent-polypeptide complex based on the detection of a label or marker are well known in the art.

In some embodiments, an epitope binding agent-based method is an immunoassay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In an embodiment, the epitope binding agent method is an immunoassay. In another embodiment, the epitope binding agent method is selected from the group consisting of an enzyme linked immunoassay (ELISA), a fluorescence based assay, a dissociation enhanced lanthanide fluoroimmunoassay (DELFIA), a radiometric assay, a multiplex immunoassay, and a cytometric bead assay (CBA). In some embodiments, the epitope binding agent-based method is an enzyme linked immunoassay (ELISA). In other embodiments, the epitope binding agent-based method is a radioimmunoassay. In still other embodiments, the epitope binding agent-based method is an immunoblot or Western blot. In alternative embodiments, the epitope binding agent-based method is an array. In another embodiment, the epitope binding agent-based method is flow cytometry. In different embodiments, the epitope binding agent-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

(c) Comparing the Amount of gdf15 Nucleic Acid or GDF15 Protein to a Reference Value The amount of gdf15 nucleic acid or GDF15 protein in the biological sample may be compared to a reference value for gdf15 nucleic acid or GDF15 protein, respectively. The subject expression levels of gdf15 nucleic acid or GDF15 protein in a biological sample are compared to a reference value for gdf15 nucleic acid or GDF15 protein, respectively, to classify a subject, determine the severity of glaucoma in a subject, determine treatment of a subject, monitor glaucoma in a subject, and/or monitor response to treatment. Generally speaking, a subject may be classified as having an increased or decreased amount of gdf15 nucleic acid or GDF15 protein compared to a reference value, wherein an increased amount of gdf15 nucleic acid or GDF15 protein is an amount above the reference value and a decreased amount is an amount equal to or below the reference value.

More specifically, the expression level of gdf15 nucleic acid or GDF15 protein is compared to the reference value of gdf15 nucleic acid or GDF15 protein to determine if gdf15 nucleic acid or GDF15 protein in the test sample is differentially expressed relative to the reference value of the gdf15 nucleic acid or GDF15 protein, respectively. The term "differentially expressed" or "differential expression" as used herein refers to a difference in the level of expression of the nucleic acids that can be assayed by measuring the level of expression of the products of the nucleic acids, such as the difference in level of messenger RNA transcript or a portion thereof expression or of proteins expressed of the nucleic acids.

The term "difference in the level of expression" refers to an increase or decrease in the measurable expression levels of gdf15 nucleic acid or GDF15 protein, for example as measured by the amount of messenger RNA transcript and/or the amount of protein in a biological sample as compared with the measureable expression level of gdf15 nucleic acid or GDF15 protein in a reference sample. In one embodiment, the differential expression can be compared using the ratio of the level of expression of gdf15 nucleic acid or GDF15 protein as compared with the expression level of gdf15 nucleic acid or GDF15 protein of a reference sample, wherein the ratio is not equal to 1.0. For example, a nucleic acid or protein is differentially expressed if the ratio of the level of expression of a first sample as compared with a second sample is greater than or less than 1.0. For example, a ratio of greater than 1, 1.2, 1.5, 1.7, 2, 3, 3, 5, 10, 15, 20 or more, or a ratio less than 1, 0.8, 0.6, 0.4, 0.2, 0.1, 0.05, 0.001 or less. In another embodiment, the differential expression is measured using p-value. For instance, when using p-value, a nucleic acid or protein is identified as being differentially expressed between a first sample and a second sample when the p-value is less than 0.1, preferably less than 0.05, more preferably less than 0.01, even more preferably less than 0.005, the most preferably less than 0.001. Depending on the sample used for the reference value, the difference in the level of expression may or may not be statistically significant. For example, if the sample used for reference value is from a subject or subjects diagnosed with glaucoma, then when the difference in the level of expression is not significantly different, the subject has glaucoma. However, when the difference in the level of expression is significantly different, the subject does not have gluacoma. Alternatively, if the sample used for reference value is from a subject or subjects diagnosed with no disease, then when the difference in the level of expression is not significantly different, the subject does not have glaucoma. However, when the difference in the level of expression is significantly different, the subject has glaucoma.

Any suitable reference value known in the art may be used. For example, a suitable reference value may be the amount of gdf15 nucleic acid or GDF15 protein in a biological sample obtained from a subject or group of subjects of the same species that have no signs or symptoms of disease (i.e. glaucoma). In another example, a suitable reference value may be the amount of gdf15 nucleic acid or GDF15 protein in a biological sample obtained from a subject or group of subjects of the same species that have not been diagnosed with disease (i.e. gluacoma). In still another example, a suitable reference value may be the amount of gdf15 nucleic acid or GDF15 protein in a biological sample obtained from a subject or group of subjects of the same species that have signs or symptoms of glaucoma. In still yet another example, a suitable reference value may be the amount of gdf15 nucleic acid or GDF15 protein in a biological sample obtained from a subject or group of subjects of the same species that have been diagnosed with glaucoma. In a different example, a suitable reference value may be the background signal of the assay as determined by methods known in the art. In another different example, a suitable reference value may be the amount of gdf15 nucleic acid or GDF15 protein in a non-diseased sample stored on a computer readable medium. In still another different example, a suitable reference value may be the amount of gdf15 nucleic acid or GDF15 protein in a diseased sample stored on a computer readable medium. Common forms of computer-readable media include, for example, a floppy disk, a flexible disk, hard disk, magnetic tape, or other magnetic medium, a CD-ROM, CDRW, DVD, or other optical medium, punch cards, paper tape, optical mark sheets, or other physical medium with patterns of holes or other optically recognizable indicia, a RAM, a PROM, and EPROM, a FLASH-EPROM, or other memory chip or cartridge, a carrier wave, or other medium from which a computer can read.

In other examples, a suitable reference value may be the amount of gdf15 nucleic acid or GDF15 protein in a reference sample obtained from the same subject. The reference sample may or may not have been obtained from the subject when glaucoma was not suspected. A skilled artisan will appreciate that that is not always possible or desirable to obtain a reference sample from a subject when the subject is otherwise healthy. For example, in an acute setting, a reference sample may be the first sample obtained from the subject at presentation. In another example, when monitoring effectiveness of a therapy, a reference sample may be a sample obtained from a subject before therapy began. In such an example, a subject may have suspected glaucoma but may not have other symptoms of glaucoma or the subject may have suspected glaucoma and one or more other symptom of glaucoma.

In a specific embodiment, a reference value may be the amount of GDF15 protein in a non-diseased sample. For example, a suitable reference value for GDF15 protein may be about 10 pg/ml, about 11 pg/ml, about 12 pg/ml, about 13 pg/ml, about 14 pg/ml, about 15 pg/ml, about 16 pg/ml, about 17 pg/ml, about 18 pg/ml, about 19 pg/ml or about 20 pg/ml. Specifically, data presented in the Examples shows that a subjects without glaucoma had an average GDF15 of 8.9±SE 7.7 pg/ml. According to the disclosure, the amount of GDF15 protein above the reference value indicates Grade I, Grade II or Grade III glaucoma. For example, an amount of GDF15 protein of about 20 pg/ml to about 80 pg/ml indicates Grade I glaucoma; an amount of GDF15 protein of about 80 pg/ml to about 160 pg/ml indicates Grade II glaucoma; and an amount of GDF15 protein of about 160 pg/ml or greater indicates Grade III glaucoma. It is to be understood that these values may change due to additional experimental data. In an exemplary embodiment, an amount of GDF15 protein of about 46.4±12.1 pg/ml indicates Grade I glaucoma; an amount of GDF15 protein of about 129.5±38.0 pg/ml indicates Grade II glaucoma; and an amount of GDF15 protein of about 190±48.7 pg/ml or greater indicates Grade III glaucoma.

An increased amount of gdf15 nucleic acid or GDF15 protein relative to a reference value indicates an increased severity of glaucoma. Specifically, a subject may have Grade I glaucoma when the amount of GDF15 protein is greater than about 10 pg/ml and less than about 80 pg/ml. In certain embodiments, a subject may have Grade I glaucoma when the amount of GDF15 protein is greater than about 9, about 10, about 11, about 12, about 13, about 14, about 15, about 16, about 17, about 18, about 19, or about 20 pg/ml and less than about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, or about 80 pg/ml. In an embodiment, a subject may have Grade I glaucoma when the amount of GDF15 protein is greater than about 10 pg/ml and less than about 50 pg/ml, greater than about 20 pg/ml and less than about 50 pg/ml, greater than about 10 pg/ml and less than about 60 pg/ml, greater than about 20 pg/ml and less than about 60 pg/ml, greater than about 10 pg/ml and less than about 70 pg/ml, greater than about 20 pg/ml and less than about 70 pg/ml, greater than about 10 pg/ml and less than about 80 pg/ml, or greater than about 20 pg/ml and less than about 80 pg/ml. In a specifc embodiment, a subject may have Grade I glaucoma when the amount of GDF15 protein is greater than about 20 pg/ml and less than about 80 pg/ml Alternatively, a subject may have Grade II glaucoma when the amount of GDF15 protein is between about 50 pg/ml and about 180 pg/ml. In certain embodiments, a subject may have Grade II glaucoma when the amount of GDF15 protein is between about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 87, about 88, about 89, or about 90 pg/ml and about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, or about 180 pg/ml. In an embodiment, a subject may have Grade II glaucoma when the amount of GDF15 protein is greater than about 50 pg/ml and less than about 170 pg/ml, greater than about 50 pg/ml and less than about 160 pg/ml, greater than about 50 pg/ml and less than about 150 pg/ml, greater than about 60 pg/ml and less than about 180 pg/ml, greater than about 60 pg/ml and less than about 170 pg/ml, greater than about 60 pg/ml and less than about 160 pg/ml, greater than about 60 pg/ml and less than about 150 pg/ml, greater than about 70 pg/ml and less than about 180 pg/ml, greater than about 70 pg/ml and less than about 170 pg/ml, greater than about 70 pg/ml and less than about 160 pg/ml, greater than about 70 pg/ml and less than about 150 pg/ml, greater than about 80 pg/ml and less than about 180 pg/ml, greater than about 80 pg/ml and less than about 170 pg/ml, greater than about 80 pg/ml and less than about 160 pg/ml, greater than about 80 pg/ml and less than about 150 pg/ml, greater than about 90 pg/ml and less than about 180 pg/ml, greater than about 90 pg/ml and less than about 170 pg/ml, greater than about 90 pg/ml and less than about 160 pg/ml, or greater than about 90 pg/ml and less than about 150 pg/ml. In a specific embodiment, a subject may have Grade II glaucoma when the amount of GDF15 protein is greater than about 80 pg/ml and less than about 160 pg/ml.

Further, a subject may have Grade III glaucoma when the amount of GDF15 protein is greater than 160 pg/ml. In certain embodiments, a subject may have Grade III glaucoma when the amount of GDF15 protein is greater than about 140, about 145, about 150, about 155, about 160, about 165, about 170, about 175, about 180, about 185, about 190, about 195, about 200, about 205, about 210, about 215, about 220, about 225, about 230, about 235, or about 240 pg/ml. In a specific embodiment, a subject may have Grade III glaucoma when the amount of GDF15 protein is greater than about 140 pg/ml.

(d) Treatment

The determination of severity of glaucoma may be used to select treatment for glaucoma subjects. As explained herein, gdf15 nucleic acid and GDF15 protein can classify a subject as having Grade I, Grade II or Grade II glaucoma and into groups that might benefit from therapy or determine the appropriate glaucoma treatment for the subject. In an embodiment, a subject classified as having Grade I, Grade II or Grade III glaucoma may be treated. A skilled artisan would be able to determine standard treatment for Grade I, Grade II or Grade III glaucoma. Accordingly, the methods disclosed herein may be used to select treatment for glaucoma subjects. In an embodiment, the subject is treated based on the difference in amount of gdf15 nucleic acid and GDF15 protein relative to the reference value. This classification may be used to identify groups that are in need of treatment or not or in need of more aggressive treatment. The term "treatment" or "therapy" as used herein means any treatment suitable for the treatment of glaucoma. Treatment may consist of standard treatments for glaucoma. Non-limiting examples of standard treatment for glaucoma include eye drops, pills, laser surgery, incisional surgery or a combination of these methods. Generally, eye drops are used to treat low grade glaucoma. If eye drops do not sufficiently control IOP, pills may be used in addition to eye drops. When medications do not achieve the desired results or have intolerable side effect, surgery may be the next option. Surgery may be laser surgery or incisional surgery. Laser surgery is viewed as an intermediate step between medication and incisional surgery. Non-limiting examples of laser surgery include argon laser trabeculoplasty (ALT), selective laser trabeculoplasty (SLT), laser peripheral iridotomy (LPI), and cycloablation Non-limiting examples of incisional surgery include trabeculectomy, drainage implant surgery, nonpenetrating surgery, ExPress mini glaucoma shunt, Trabectome and canaloplasty. Based on the classification into Grade I, Grade II or Grade III based on the amount of gdf15 nucleic acid or GDF15 protein in a biological sample, the subject may be treated with eye drops, pills, laser surgery and/or incisional surgery. Additionally, the treatment decision may be made based on evidence of progression from one Grade to the next.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

There are currently no available biomarkers which detect glaucoma severity or progression. Although Tgfb2 can cause glaucoma, it is not a biomarker for glaucoma. Currently, treatment for glaucoma is decided based on intraocular pressure (IOP) and perimetry. However, IOP is largely variable from patient to patient and perimetry is a subjective test. Thus, a biomarker to aid in treatment decisions for glaucoma is needed.

Figure 2:
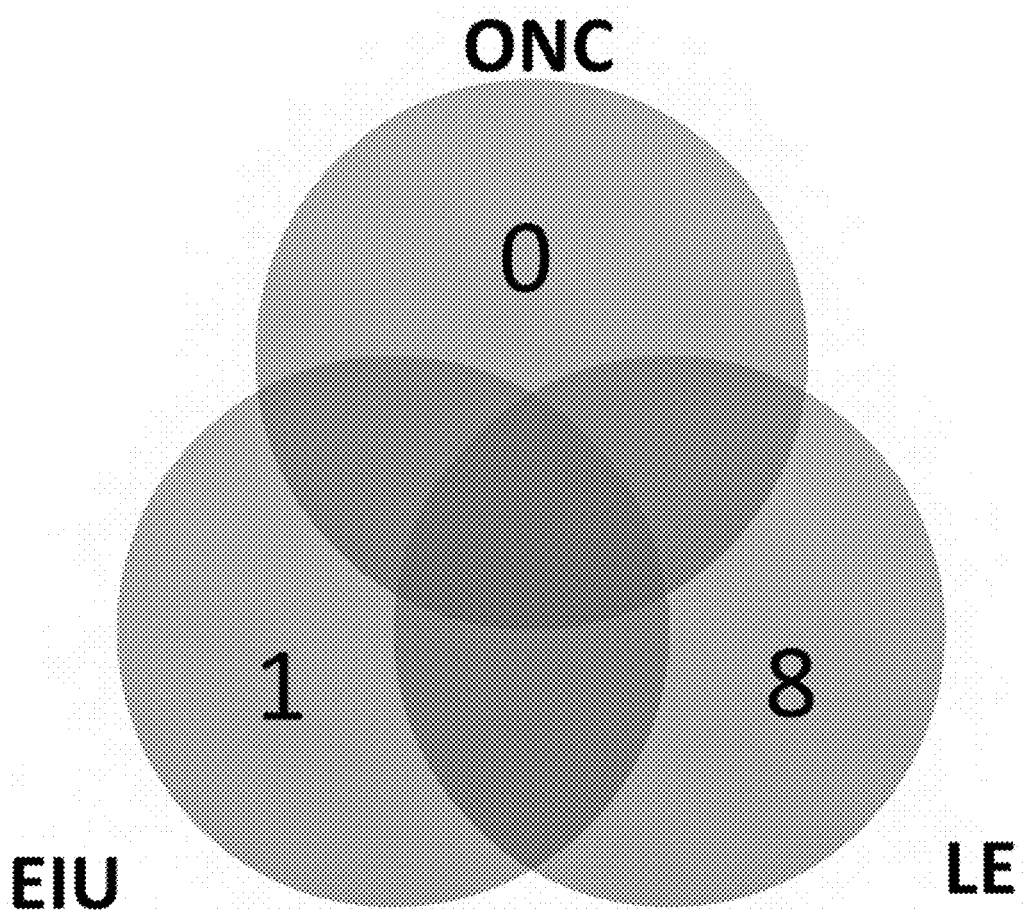
FIG. 2 depicts a Venn diagram showing the downregulated genes that overlap between ONC, EIU and LE.

In order to identify a biomarker for glaucoma, the inventors sought to identify a biomarker that reflects retinal ganglion cell (RGC) death. Tears, aqueous humor, vitreous and serum (plasma) were examined. A cytokine array which evaluated 88 genes was conducted using different retinal cell death models (Table 1). Analysis of the data obtained from the cytokine array revealed that 8 genes were upregulated in the optic nerve crush model (ONC) and 0 genes were downregulated, 15 genes were upregulated in the endotoxin-induced uveitis model (EIU) and 1 gene was downregulated and 22 genes were upregulated in the light exposure induced retinal degeneration model (LE) and 8 genes were downregulated. FIG. 1 shows the upregulated genes that overlap between the different disease models. One gene is specifically upregulated in ONC, but not EIU or LE. Table 2 presents a list of these genes showing that gdf15 is only upregulated in ONC. FIG. 2 shows the downregulated genes that overlap between the different disease models and Table 3 presents a list of these genes.

TABLE 1

| 88 genes evaluated in the cytokine focused PCR array. | | | | | | |
|---|---|---|---|---|---|---|
| Chemokines | Interferons | Interleukins | Growth Factors | Tgfb superfamily | TNF superfamily | others |
| ccl2 | Ifna2 | Il10 | Cntf | Bmp1 | Cd40lg | Adipoq |
| ccl19 | Ifna4 | Il11 | Csf1(MCSF) | Bmp2 | Cd70 | Aimp1 |
|  | Ifnb1 | Il12b | Csf2(GM-CSF) | Bmp3 | Fasl | Ctf1 |
|  | Ifng | Il13 | Csf3(GCSF) | Bmp4 | Lta | Mif |
|  |  | Il15 | Fgf10 | Bmp5 | Ltb | Scgb3a1 |
|  |  | Il16 | Lefty1 | Bmp6 | Tnf | Spp1 |
|  |  | Il17a | Lif | Bmp7 | Tnfrsf11b |  |
|  |  | Il17b | Osm | Gdf2 | Tnfsf10 |  |
|  |  | Il17c | Thpo | Gdf5 | Tnfsf11 |  |
|  |  | Il17f | Vegfa | Mstn(Gdf8) | Tnfsf12 |  |
|  |  | Il18 | Vegfb | Gdf9 | Tnfsf13 |  |
|  |  | Il19 | Vegfc | Gdf15 | Tnfsf13b |  |
|  |  | Il1a | Figf(Vegfd) | Inha | Tnfsf14 |  |
|  |  | Il1b | Vegfe | Inhba | Tnfsf15 |  |
|  |  | Il1m | Pgf(Plgf) | Tgfb1 | Tnfsf18 |  |
|  |  | Il2 |  | Tgfb2 | Tnfsf4 |  |
|  |  | Il20 |  |  | Tnfsf8 |  |
|  |  | IL21 |  |  | Tnfsf9 |  |
|  |  | Il23a |  |  |  |  |
|  |  | Il24 |  |  |  |  |
|  |  | Il25(Il17e) |  |  |  |  |
|  |  | Il27 |  |  |  |  |
|  |  | Il3 |  |  |  |  |
|  |  | Il4 |  |  |  |  |
|  |  | Il5 |  |  |  |  |
|  |  | Il6 |  |  |  |  |
|  |  | Il7 |  |  |  |  |
|  |  | Il9 |  |  |  |  |
|  |  | Txlna(Il14) |  |  |  |  |

TABLE 2

Upregulated genes.

| Group 1 (only ONC) | Group 2 (only in EIU) | Group 3 (only in LE) | Group 4 (ONC and EIU) | Group 5 (LE and EIU) | Group 6 (common in 3 group) |
|---|---|---|---|---|---|
| Gdf15 | ccl19 | Il12b | Tgfb1 | Il6 | ccl2 |
| | Mstn(Gdf8) | Il7 | | Il10 | Il1a |
| | Tnfsf10 | Csf3(GCSF) | | Csf1(MCSF) | Il1b |
| | Ctf1 | Lefty1 | | Bmp2 | Pgf(Plgf) |
| | | Lif | | | Tnf |
| | | Osm | | | Scgb3a1 |
| | | Bmp1 | | | |
| | | Lta | | | |
| | | Ltb | | | |
| | | Tnfsf12 | | | |
| | | Tnfsf18 | | | |
| | | Spp1 | | | |

TABLE 3

Downregulated genes.

| Group 1 (only ONC) | Group 2 (only in EIU) | Group 3 (only in LE) |
|---|---|---|
| | Aimp1 | Il15 |
| | | Il18 |
| | | Il25(Il17e) |
| | | Vegfa |
| | | Vegfc |
| | | Bmp5 |
| | | Inhba |
| | | Tnfsf8 |

Figure 3A:
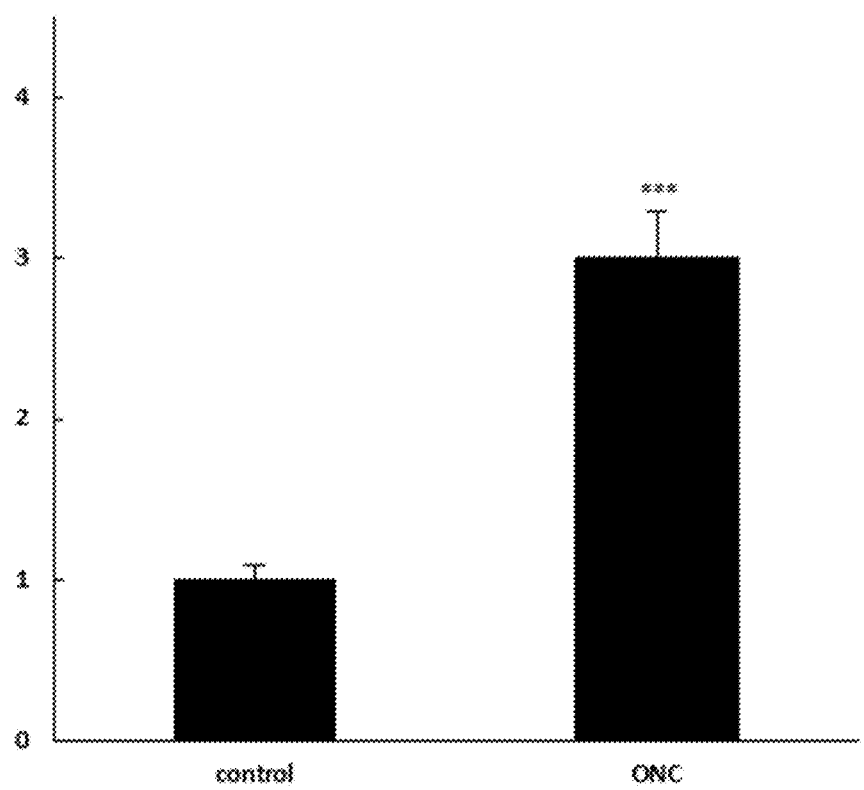
FIG. 3A, FIG. 3B and FIG. 3C depict graphs showing the gene expression levels of gdf15 in ONC (FIG. 3A), EIU (FIG. 3B) and LE (FIG. 3C). Gdg15 gene expression is only upregulated in the ONC model.
Figure 3B:
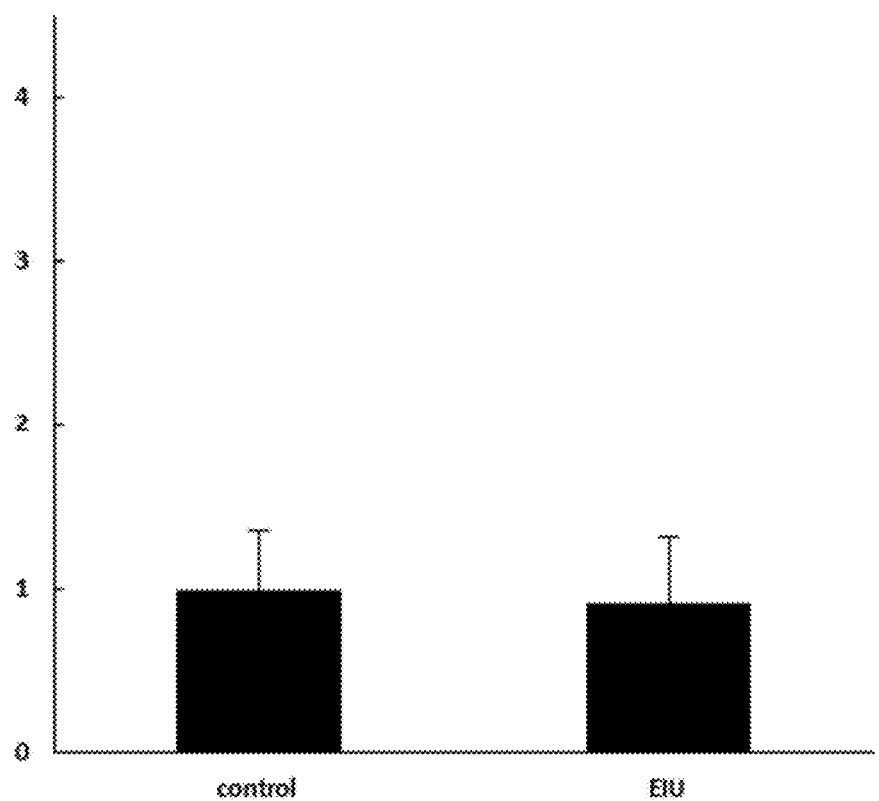
Figure 3C:
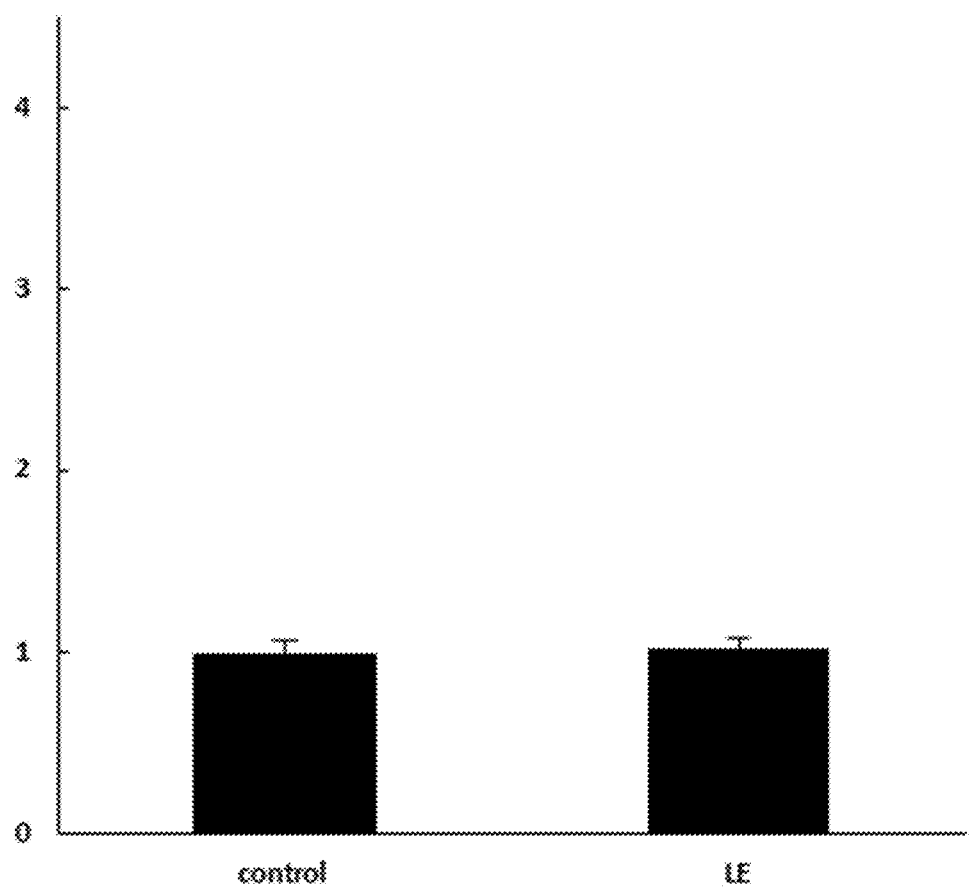
Figure 4A:
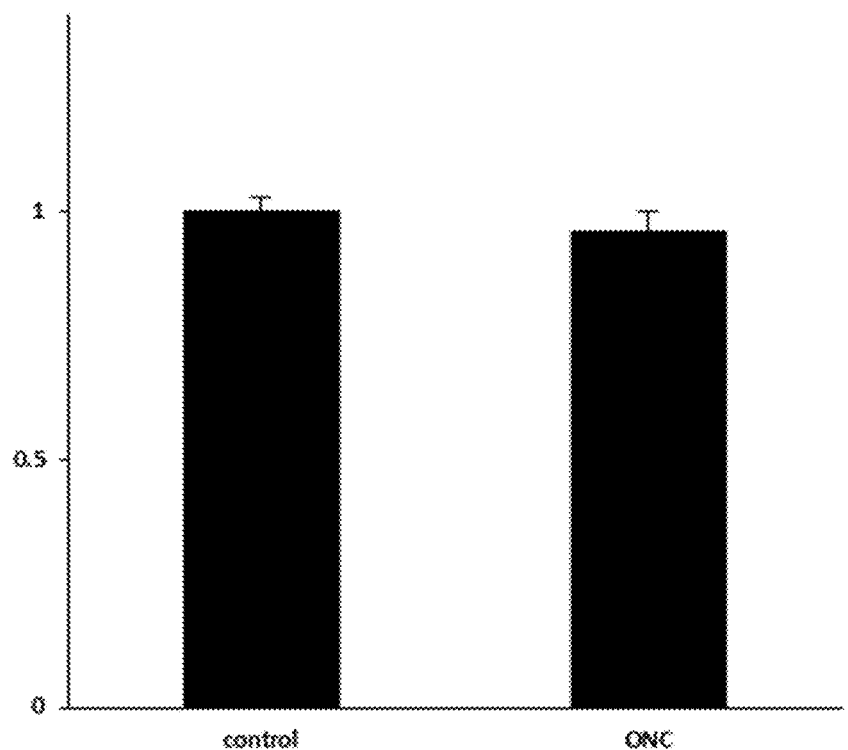
FIG. 4A, FIG. 4B and FIG. 4C depict graphs showing the gene expression levels of tgfb2 in ONC (FIG. 4A), EIU (FIG. 4B) and LE (FIG. 4C). Tgfb2 is equivalent to control in all models.
Figure 4B:
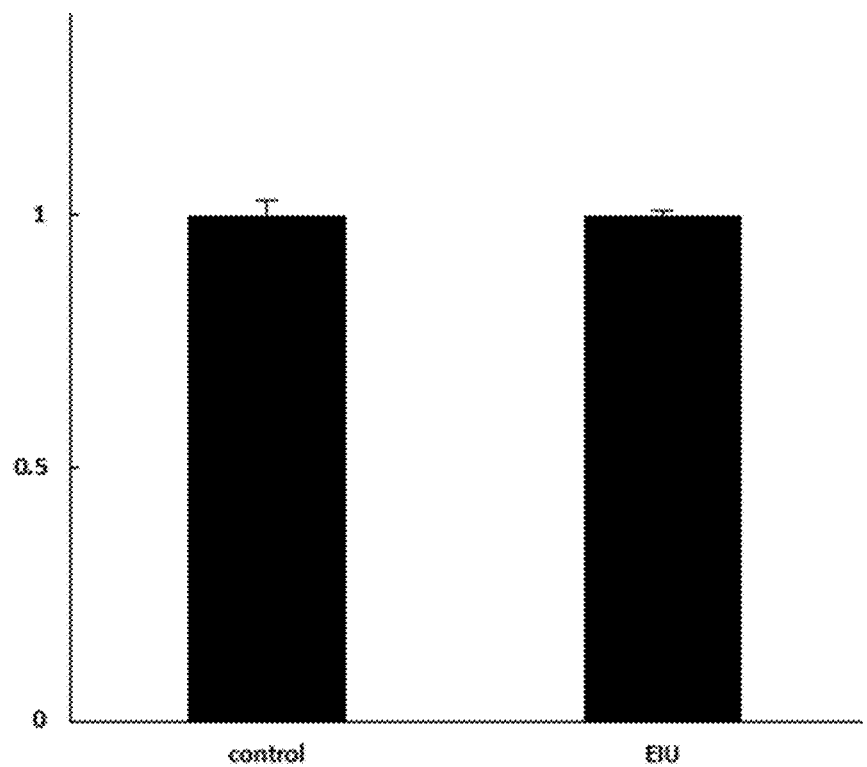
Figure 4C:
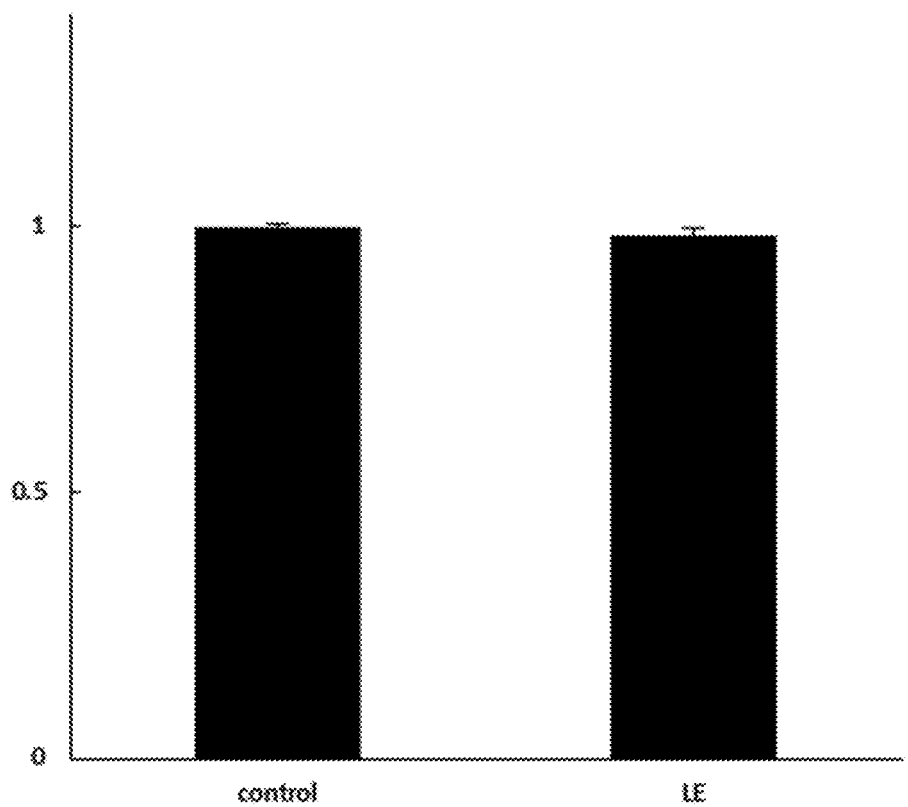
Figure 5A:
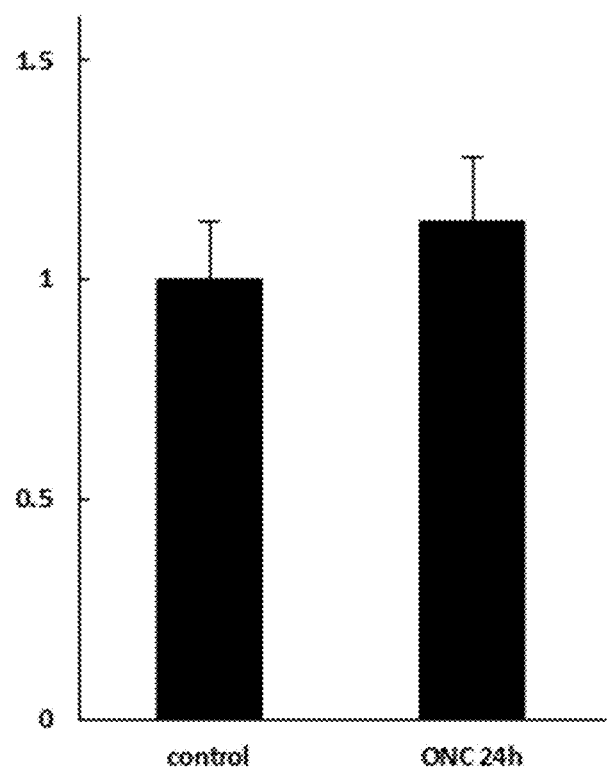
FIG. 5A, FIG. 5B, FIG. 5C, FIG. 5D, FIG. 5E, FIG. 5F, FIG. 5G, FIG. 5H, FIG. 5I and FIG. 5J depict graphs showing that none of the other gdf genes are altered in the ONC model.
Figure 5B:
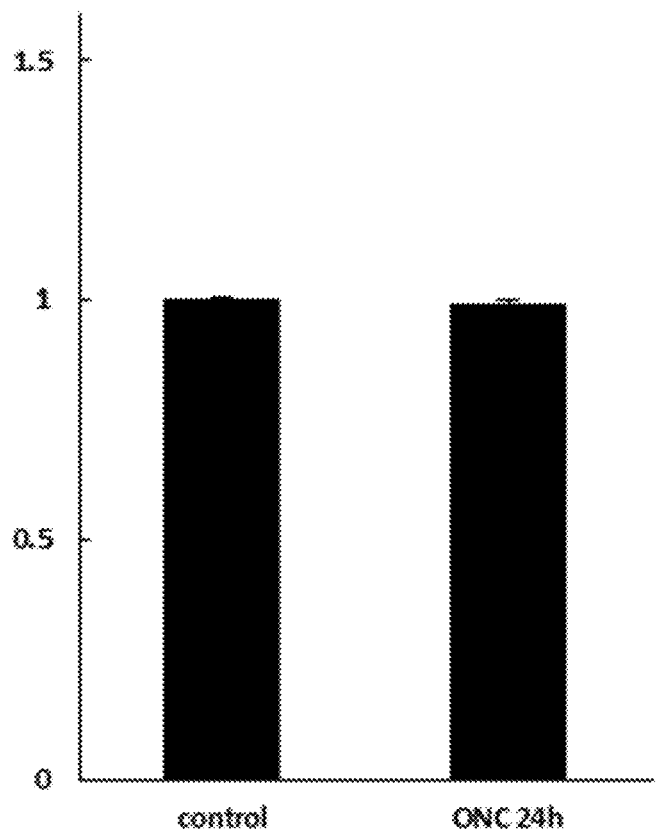
Figure 5C:
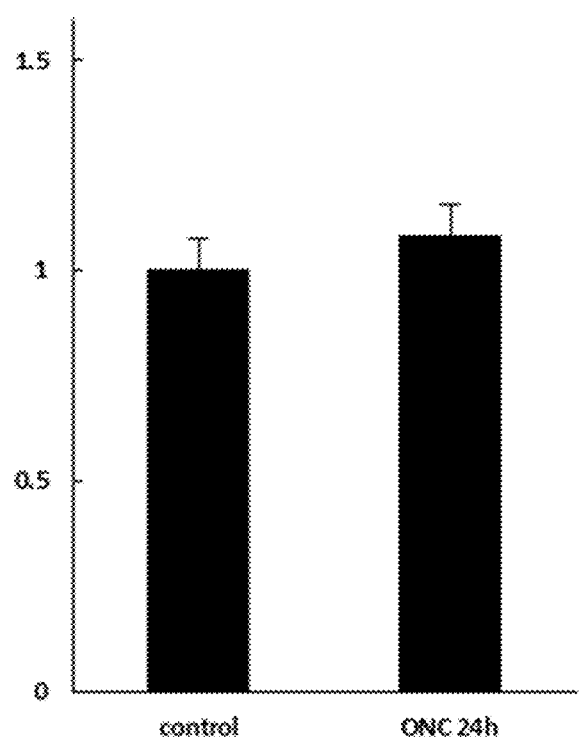
Figure 5D:
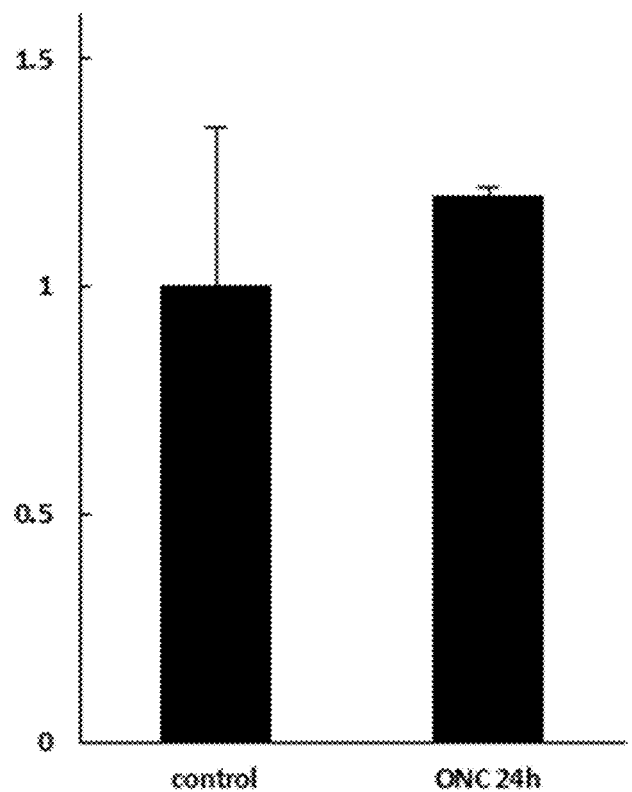
Figure 5E:
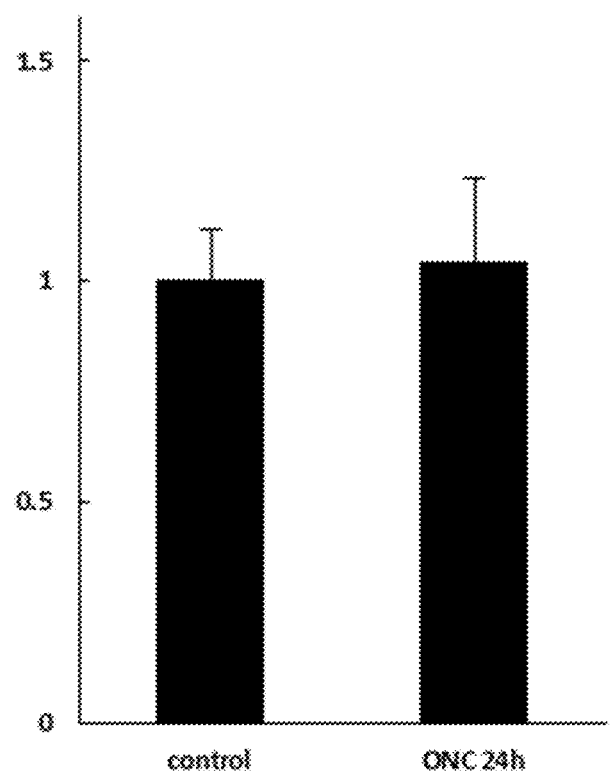
Figure 5F:
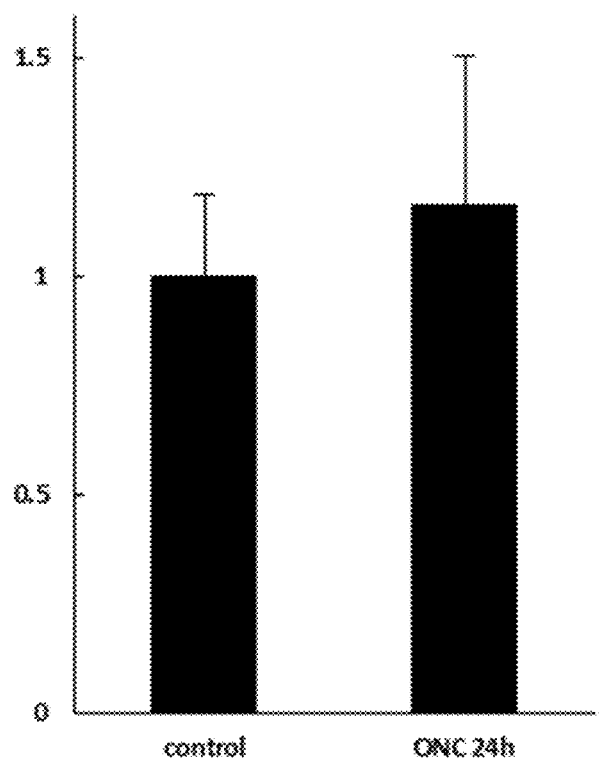
Figure 5G:
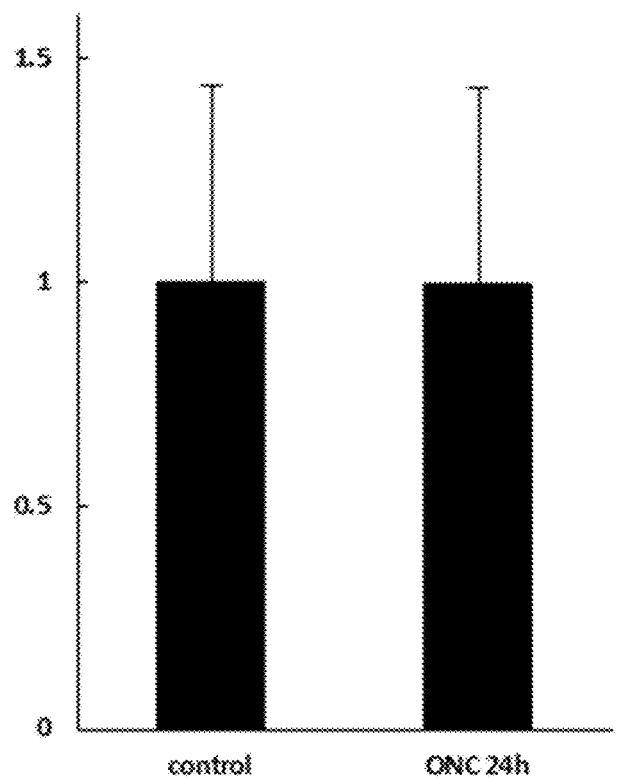
Figure 5H:
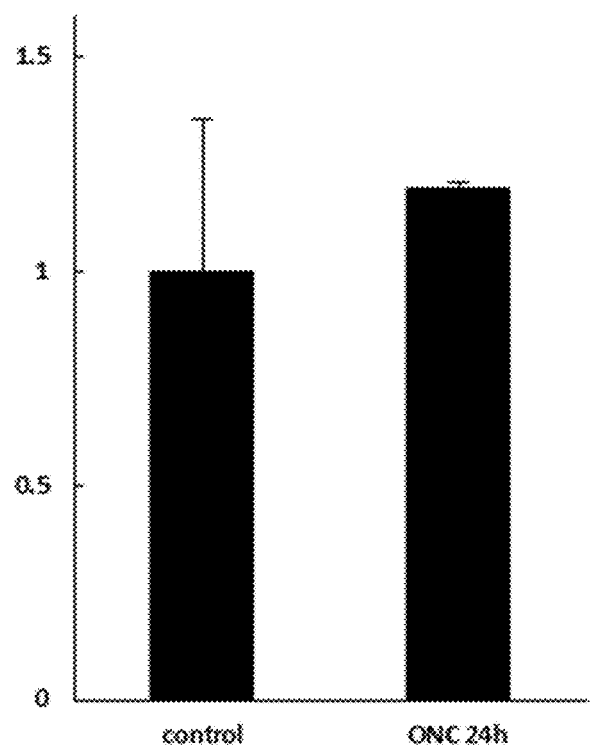
Figure 5I:
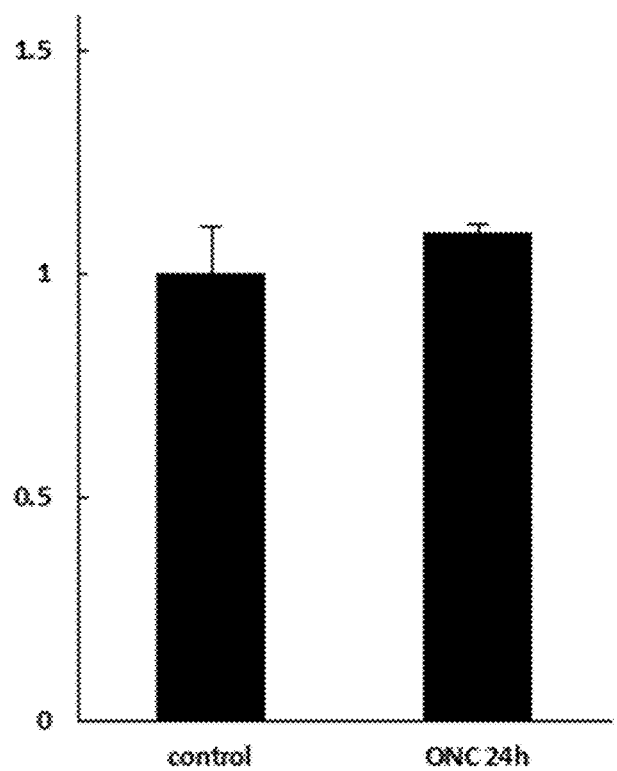
Figure 5J:
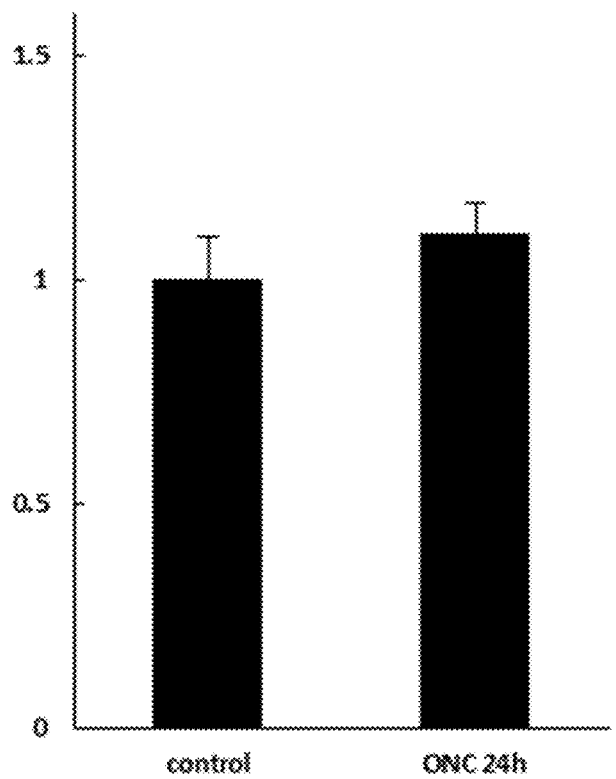

Given that gdf15 was unique to ONC, the expression profile of gdf15 was further evaluated in each of the disease models. FIG. 3 shows the gene expression levels of gdf15 in ONC (FIG. 3A), EIU (FIG. 3B) and LE (FIG. 3C). Gdg15 gene expression is only upregulated in the ONC model. In comparison, tgfb2 is equivalent to control in all models (FIG. 4A, FIG. 4B, FIG. 4C). These results confirmed that gdf15 gene expression is specific to ONC.

Gdf is part of the tgfb superfamily. To determine if other gdf family members were altered in ONC, gdf1, gdf2, gdf3, gdf5, gdf6, gdf7, gdf8, gdf9, gdf10 and gdf11 gene expression was evaluated at 24 hours in the ONC model. FIG. 5A, FIG. 5B, FIG. 5C, FIG. 5D, FIG. 5E, FIG. 5F, FIG. 5G, FIG. 5H, FIG. 5I and FIG. 5J show that none of the other gdf genes are altered in the ONC model.

Figure 6:
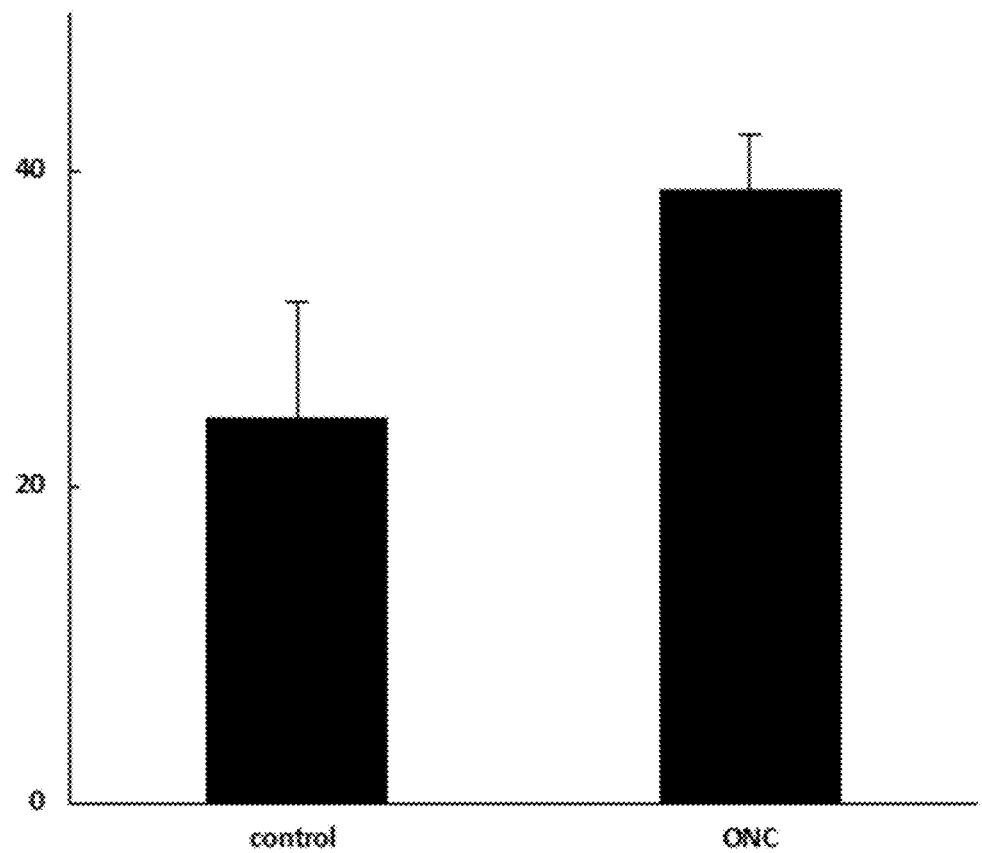
FIG. 6 depicts a graph showing GDF15 protein was elevated in the ONC mouse model.
Figure 7A:
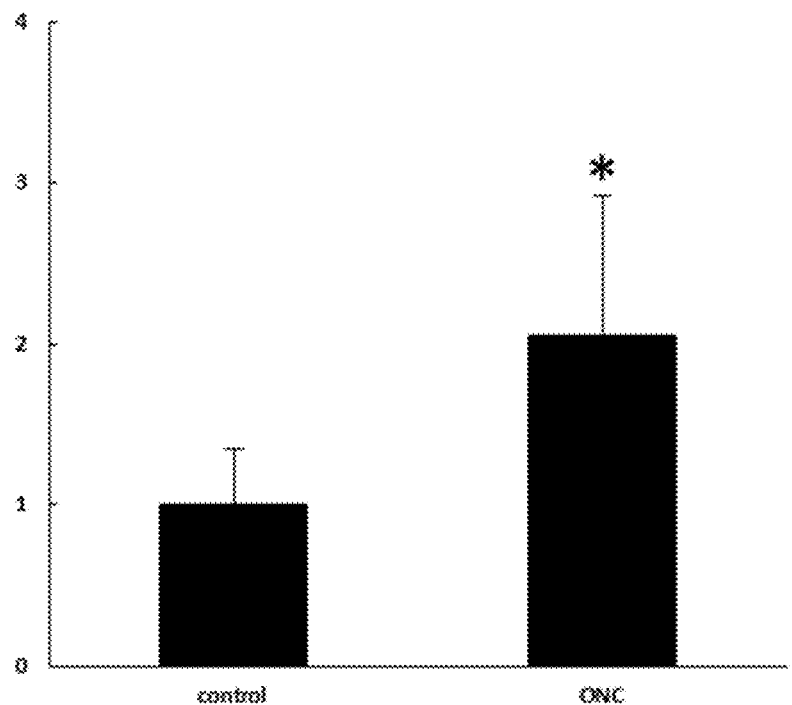
FIG. 7A and FIG. 7B depicts graphs showing that gdf15 was significantly upregulated in ONC (FIG. 7A) and tgfb2 was unchanged in ONC (FIG. 7B).
Figure 7B:
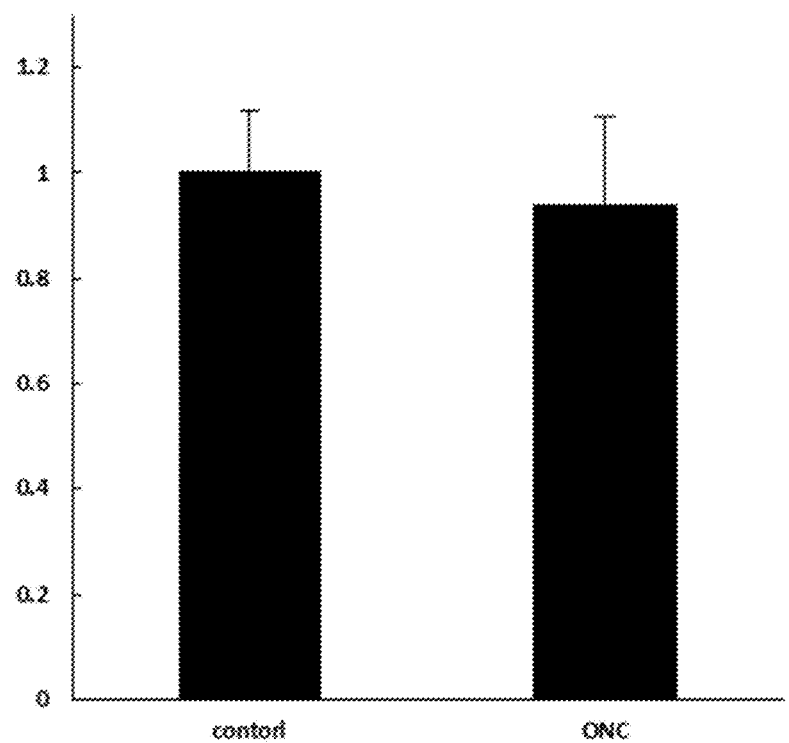
Figure 7C:
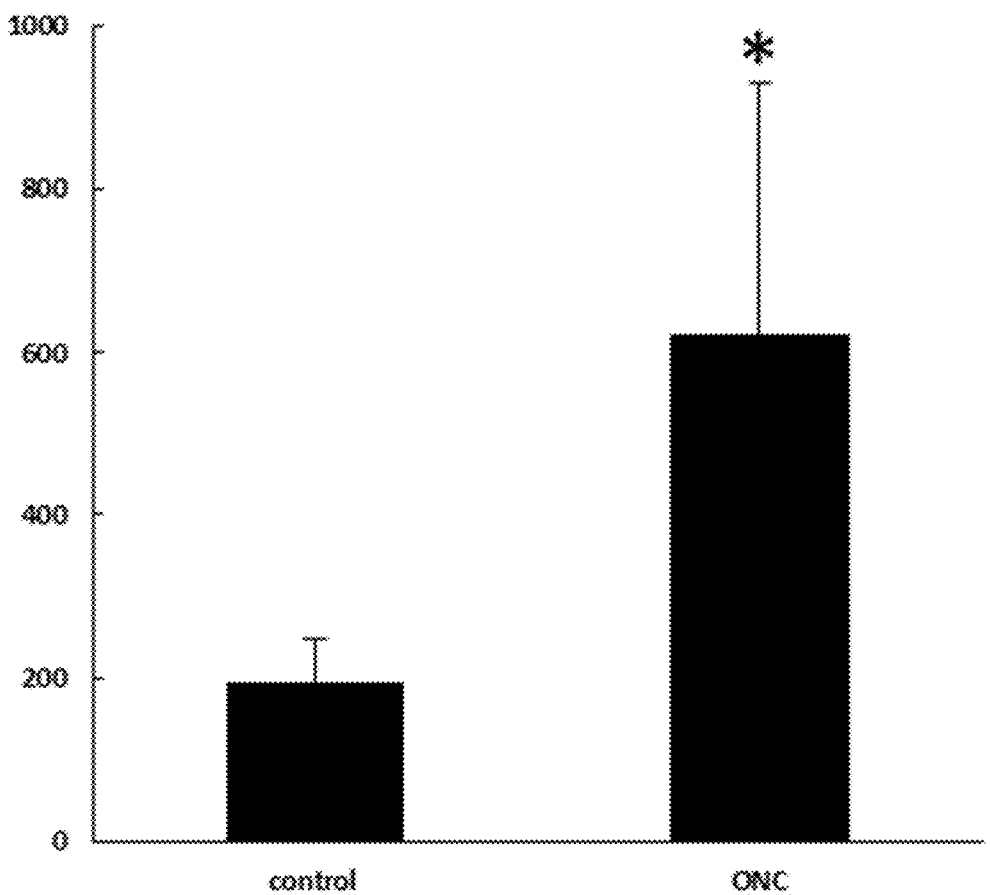
FIG. 7C depicts a graph showing that GDF15 protein expression, detected via an ELISA assay conducted on the aqueous humor, is also upregulated in the rat model of ONC.

Given that gdf15 gene expression is upregulated in ONC, it was determined if elevated GDF15 protein levels are detectable in the aqueous humor in a mouse model of ONC. Using an ELISA assay to detect GDF15 protein, it was found that GDF15 protein was elevated in the ONC mouse model (FIG. 6). GDF15 protein and gdf15 nucleic acid expression was then evaluated in a rat model of ONC. Evaluation of gdf15 and tgfb2 nucleic acid expression showed that gdf15 was significantly upregulated in ONC and tgfb2 was unchanged in ONC (FIG. 7A, FIG. 7B). Additionally, evaluation of GDF15 protein expression via an ELISA assay conducted on the aqueous humor showed that GDF15 protein is also upregulated in the rat model of ONC (FIG. 7C).

Figure 8A:
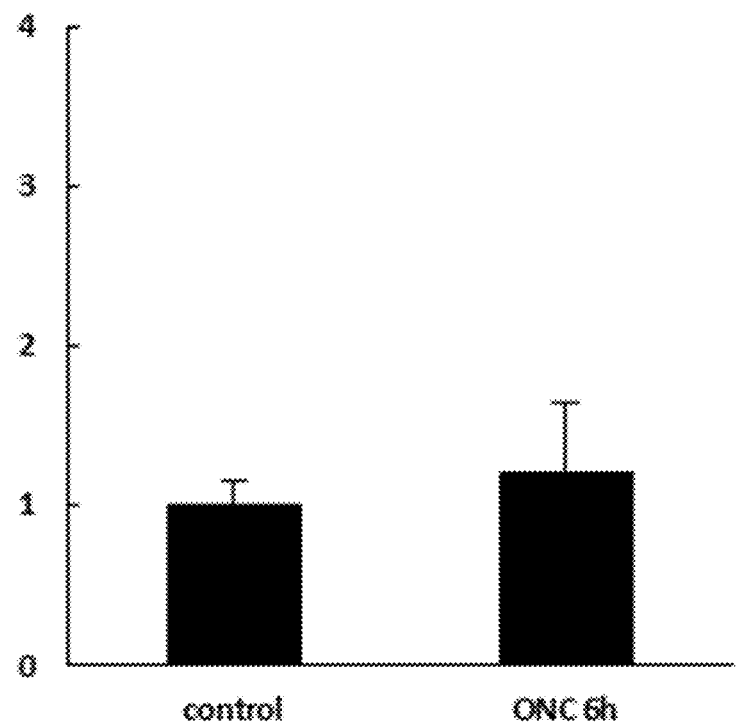
FIG. 8A, FIG. 8B and FIG. 8C depict graphs showing the expression at 6 hours of gdf15 in the anterior segment, lens and retina, respectively. Results showed that there was no significant upregulation in any eye tissue.
Figure 8B:
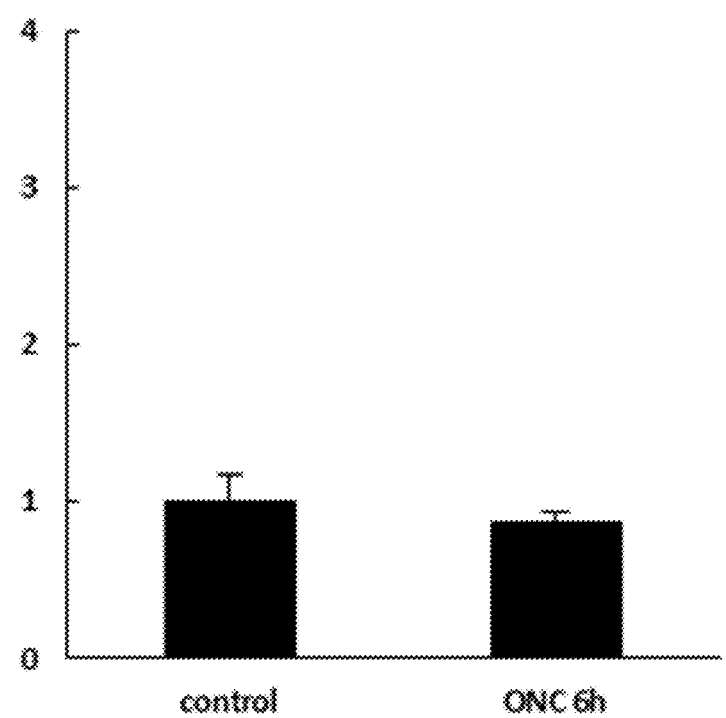
Figure 8C:
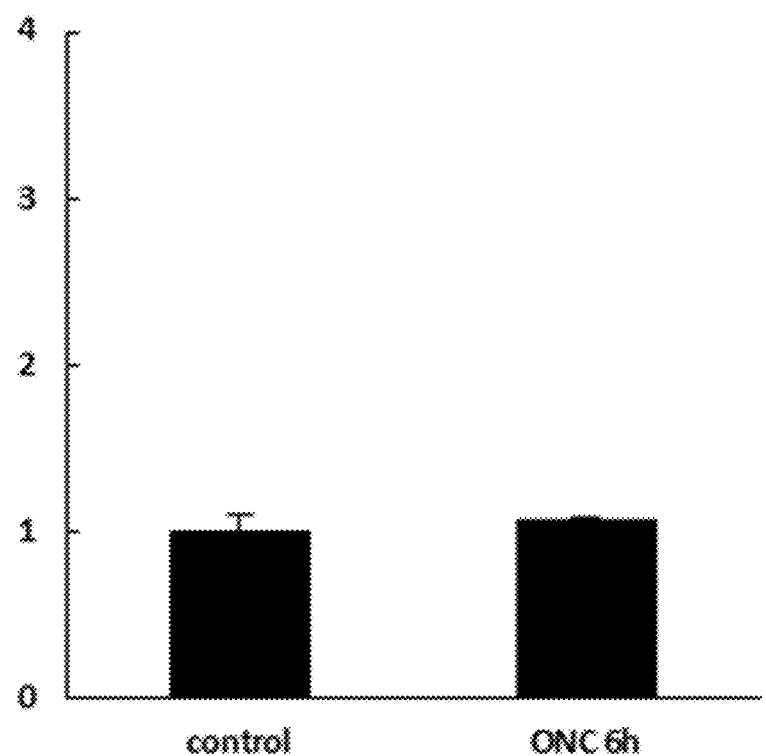
Figure 8D:
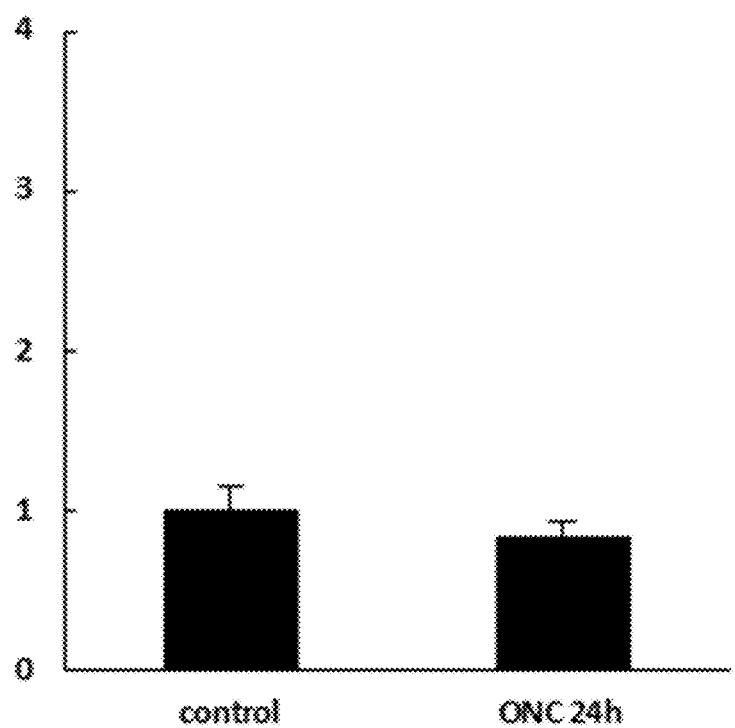
FIG. 8D, FIG. 8E and FIG. 8F depict graphs showing that gdf15 expression was significantly upregulated in the retina (FIG. 8F), but not in the anterior segment or the lens (FIG. 8D, FIG. 8E, respectively).
Figure 8E:
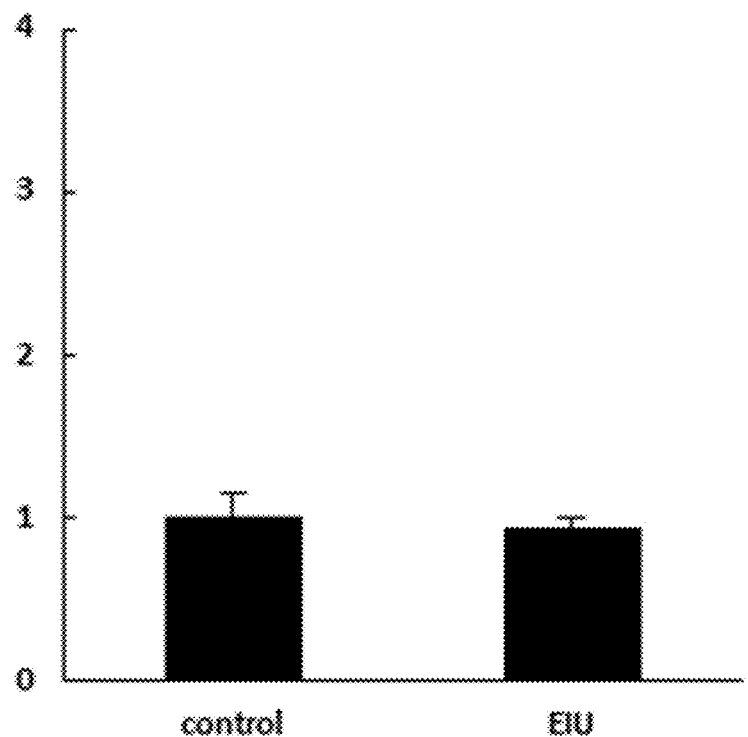
Figure 8F:
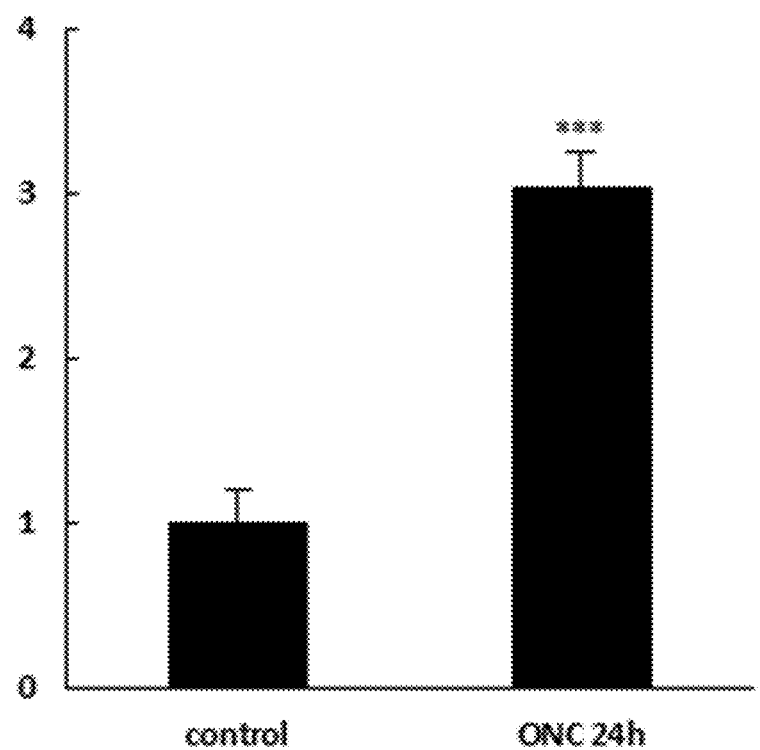
Figure 12:
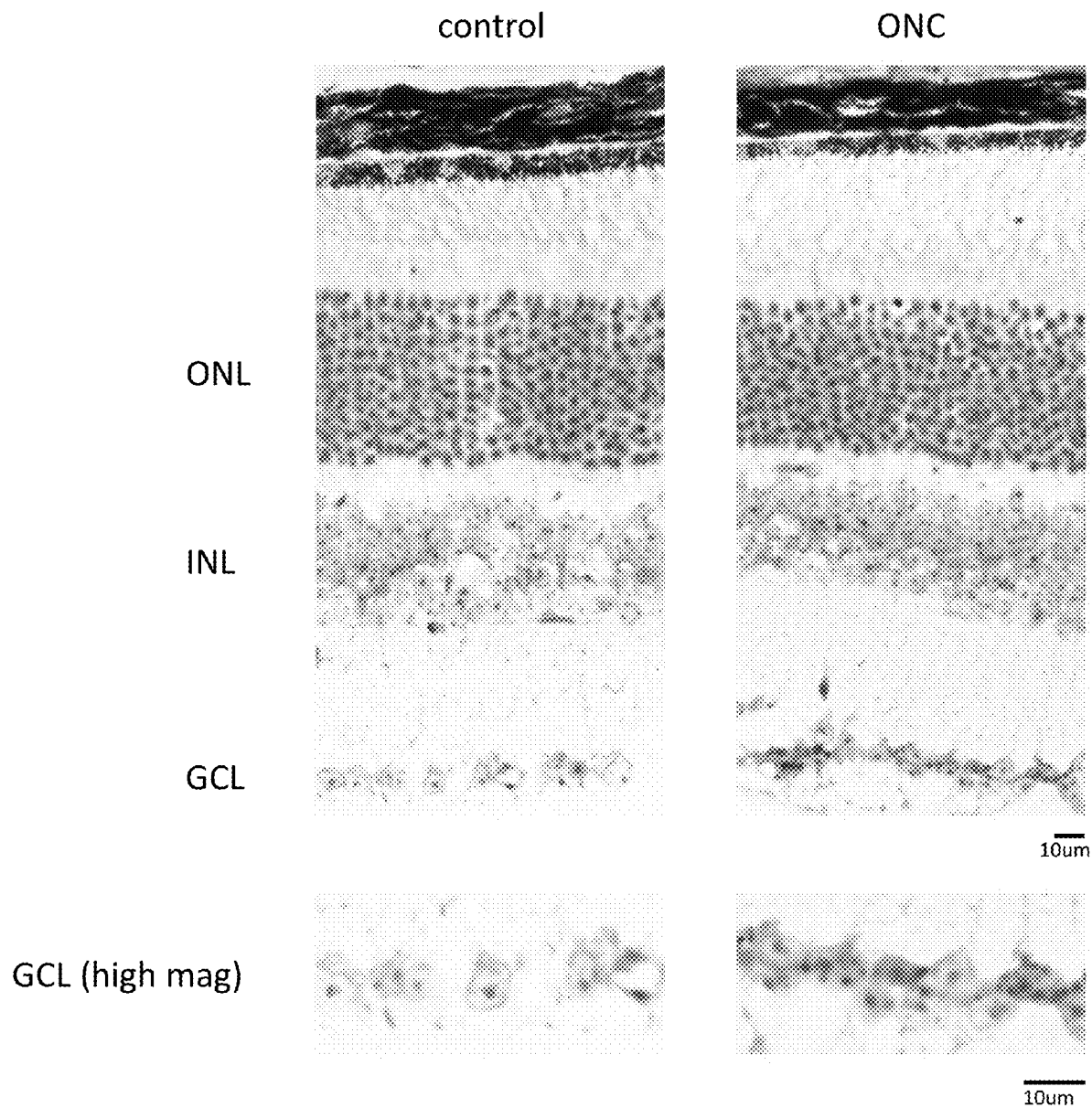
FIG. 12 depicts an image showing in situ hybridization (ISH) of control tissue and ONC tissue. i GDF15 is specifically upregulated in the ganglion cell layer (GCL) relative to the outer nuclear layer (ONL) and inner nuclear layer (INL) in the ONC tissue.

Gdf15 nucleic acid expression was then evaluated in various regions within the eye. Specifically, the expression of gdf15 in the anterior segment, lens and retina was evaluated. Results showed that at 6 hours there was no significant upregulation in any eye tissue (FIG. 8A, FIG. 8B, FIG. 8C). However, at 24 hours, gdf15 expression was significantly upregulated in the retina (FIG. 8F), but not in the anterior segment or the lens (FIG. 8D, FIG. 8E, respectively). These data suggest that gdf15 expression is specific to the retina. Further, using in situ hybridization (ISH), it is readily observed that GDF15 is specifically upregulated in the ganglion cell layer (GCL) relative to the outer nuclear layer (ONL) and inner nuclear layer (INL) in the ONC model (FIG. 12).

Figure 9A:
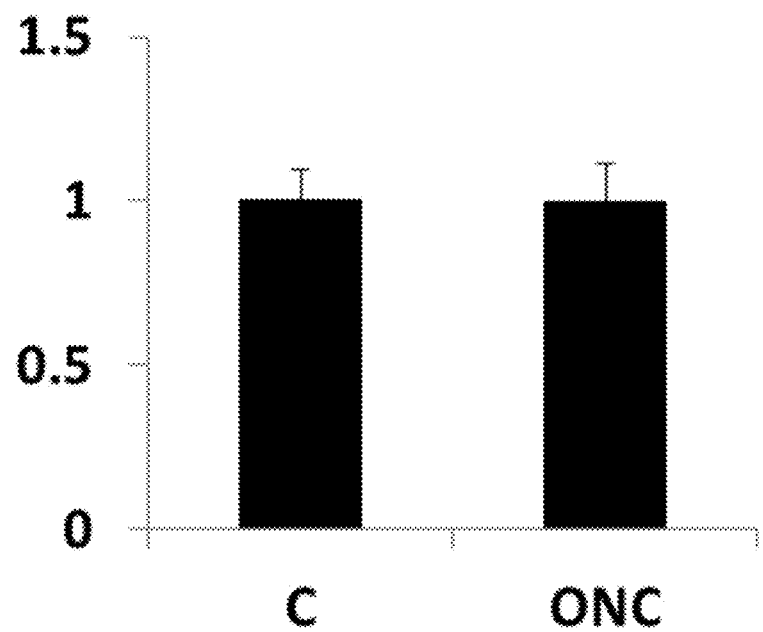
FIG. 9A depicts a graph showing that there is no significant difference in macrophages in the control versus the ONC model.
Figure 9B:
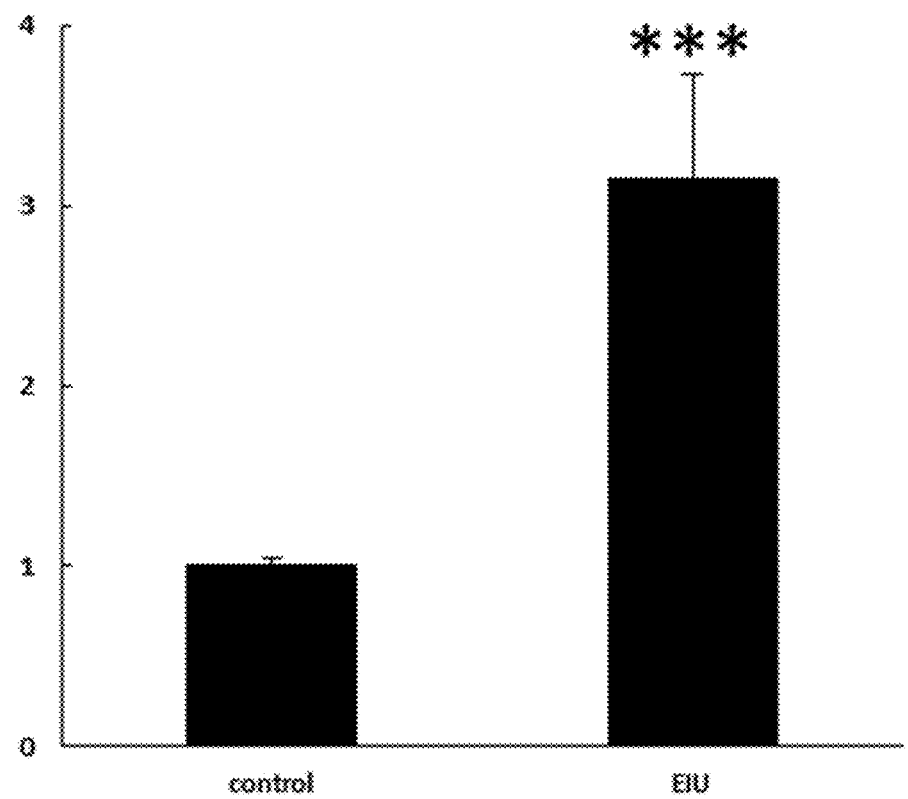
FIG. 9B and FIG. 9C depict graphs showing that both the EIU and LE models, respectively, show a significant increase in macrophages relative to control.
Figure 9C:
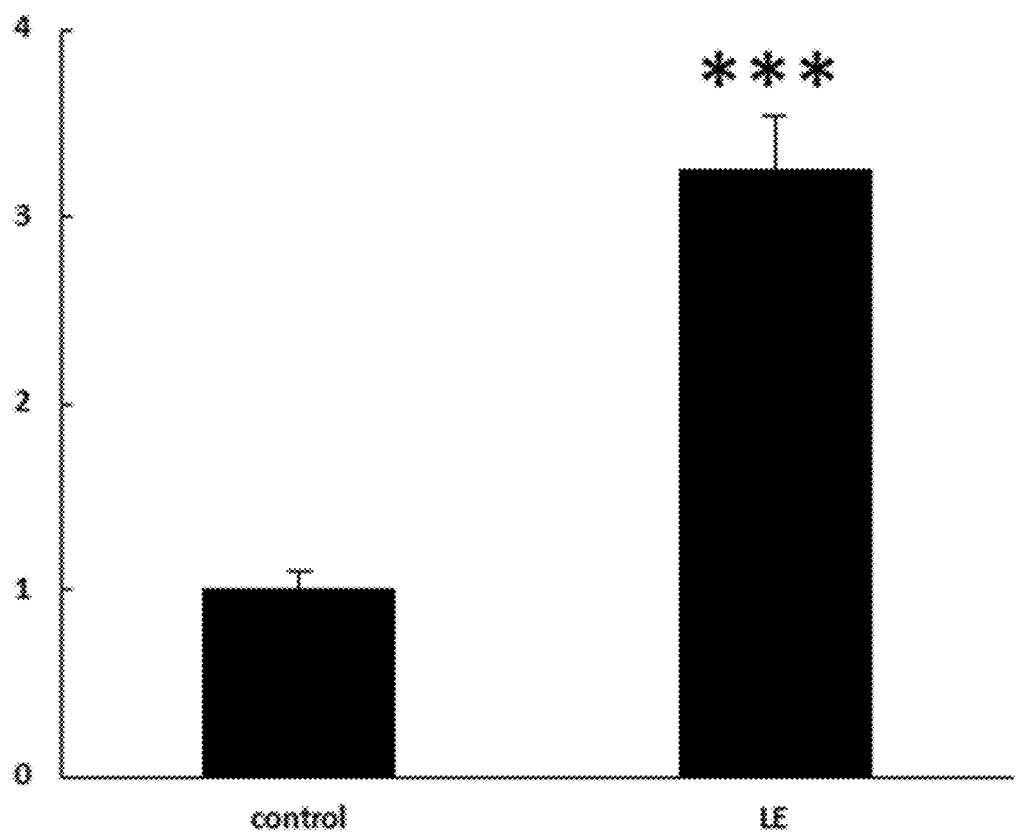

It was next determined if GDF15 expression could be linked to an increase in macrophages in the disease model. F4/80 antigen was used to detect macrophages. FIG. 9A shows that there is no significant difference in macrophages in the control versus the ONC model. In contrast, both the EIU and LE models show a significant increase in macrophages relative to control (FIG. 9B, FIG. 9C, respectively).

Figure 10:
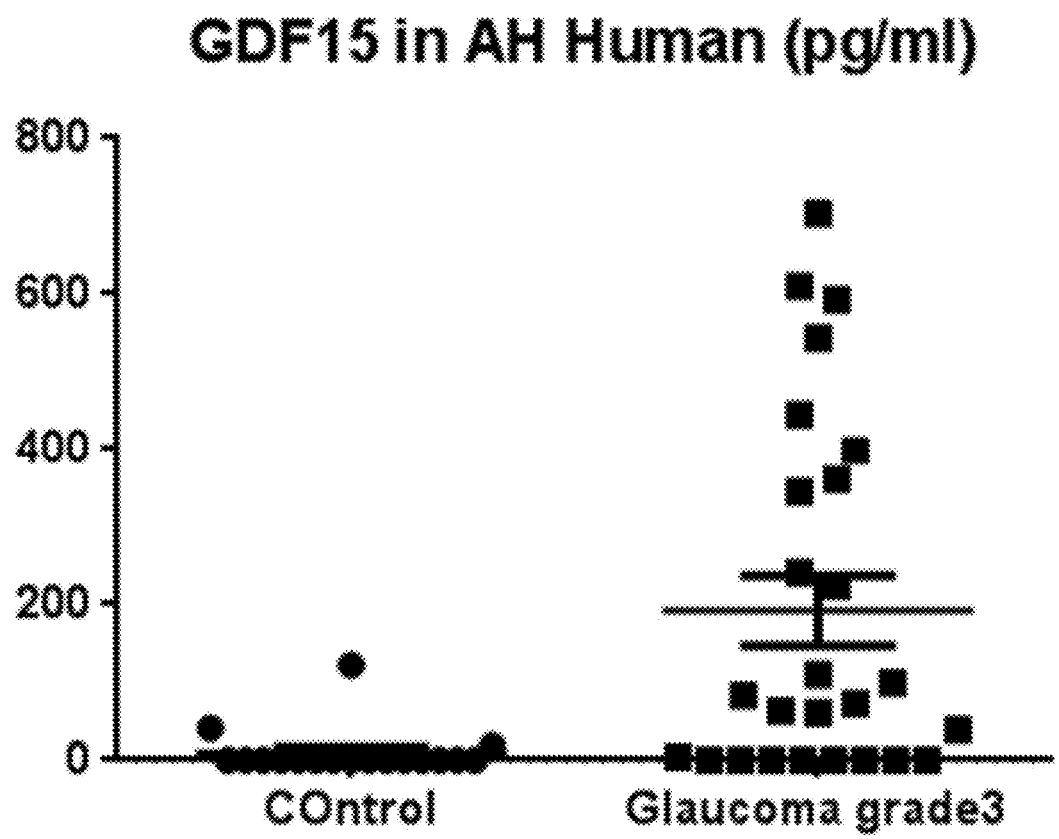
FIG. 10 depicts a graph showing that there is a significant increase in GDF15 expression in the glaucoma patients relative to control patients.
Figure 11:
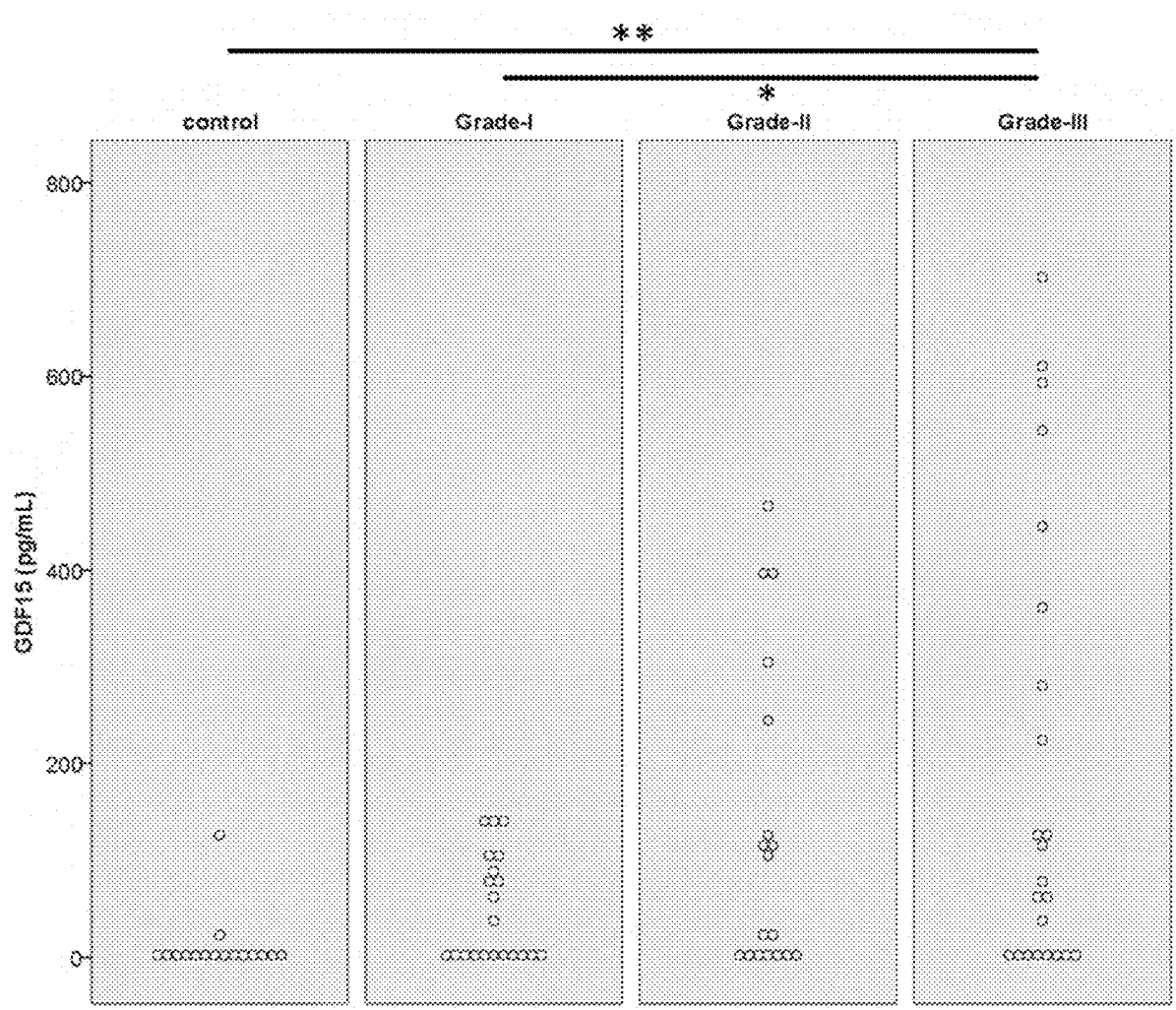
FIG. 11 depicts a graph showing that GDF15 expression correlates with disease severity. As the severity of glaucoma progresses from Grade I to Grade II to Grade III, the amount of GDF15 detected increases. Turkey multiple comparison *p<0.05 **p<0.01.

The crushed nerve model is a model of acute injury to retinal ganglion cells. Although this model is used to study glaucoma, it cannot be known that this model recapitulates what occurs in glaucoma as glaucoma is a chronic disease and thus results in chronic injury to retinal ganglion cells. Thus, since it cannot be known that upregulation of GDF15 in ONC translates to upregulation in human glaucoma, human samples were evaluated for GDF15 protein expression. Aqueous humor was collected from glaucoma patients and the amount of GDF15 was measured by ELISA. FIG. 10 shows that there was a significant increase in GDF15 expression in the glaucoma patients relative to control patients. Accordingly, these results were able to show that GDF15 is upregulated in human glaucoma. Importantly, we showed that GDF15 expression correlated with disease severity (FIG. 11). As the severity of glaucoma progressed from Grade I to Grade II to Grade III, the amount of GDF15 detected increased. Accordingly, these results demonstrate that GDF15 will be a sensitive and specific marker of glaucoma progression and will guide therapeutic decision making.

What is claimed is:

1. A method of monitoring response to glaucoma treatment in a subject, wherein the subject is a mammal, the method comprising:
    a) measuring the amount of GDF15 protein in a first biological sample obtained from the subject;
    b) treating the subject with prescription eye drops, laser surgery, or incisional surgery;
    c) measuring the amount of GDF15 protein in a second biological sample obtained from the subject at a later time;
    d) comparing the amount of GDF15 protein in the first biological sample to the amount of GDF15 protein in the first biological sample; and
    e) determining response to treatment if the amount of GDF15 protein in the second biological sample is increased, the same, or decreased relative to the amount of GDF15 protein in the first biological sample, wherein the first and second biological sample is selected from tears, aqueous humor, vitreous, serum, or retinal tissue and wherein, if the amount of GDF15 protein in the second biological sample is increased or the same, the treatment is altered.

2. The method of claim 1, wherein the amount of GDF15 protein above the reference value indicates Grade I, Grade II or Grade III glaucoma.

3. The method of claim 2, wherein an amount of GDF15 protein of about 20 pg/ml to about 80 pg/ml indicates Grade I glaucoma; an amount of GDF15 protein of about 80 pg/ml to about 160 pg/ml indicates Grade II glaucoma; and an amount of GDF15 protein of about 160 pg/ml or greater indicates Grade III glaucoma.

4. The method of claim 2, wherein an amount of GDF15 protein of about 46.4±12.1 pg/ml indicates Grade I glaucoma; an amount of GDF15 protein of about 129.5±38.0 pg/ml indicates Grade II glaucoma; and an amount of GDF15 protein of about 190±48.7 pg/ml or greater indicates Grade III glaucoma.

5. The method of claim 1, wherein the amount of GDF15 protein is detected by contacting the sample with an antibody specific for GDF15 and quantifying the amount of GDF15 bound to the antibody.

6. The method of claim 5, wherein the amount of GDF15 protein is detected by a method selected from the group consisting of an immunoassay, an enzyme linked immunoassay (ELISA), a fluorescence based assay, a dissociation enhanced lanthanide fluoroimmunoassay (DELFIA), a radiometric assay, a multiplex immunoassay, and a cytometric bead assay (CBA).

7. The method of claim 6, wherein the amount of GDF15 protein is detected by an ELISA.

8. The method of claim 1, further comprising assessing clinical symptoms, determining intraocular pressure, performing perimetry, or a combination thereof.

* * * * *